US011352627B2

(12) United States Patent
Bourdoulous et al.

(10) Patent No.: US 11,352,627 B2
(45) Date of Patent: Jun. 7, 2022

(54) TREATMENT OF HER-2 DEPENDENT CANCER USING AN AGENT THAT MODULATES THE ACTIVITY OF A MIRNA

(71) Applicants: UNIVERSITE DE PARIS, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S.), Paris (FR)

(72) Inventors: Sandrine Bourdoulous, Gagny (FR); Anaïs Domingot, Paris (FR); Camille Faure, Paris (FR)

(73) Assignees: INSTITUT NATIONAL DE LA SANTE ET DE LA RECHERCHE MEDICAL (INSERM), Paris (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 119 days.

(21) Appl. No.: 16/758,274

(22) PCT Filed: Oct. 24, 2018

(86) PCT No.: PCT/EP2018/079212
§ 371 (c)(1),
(2) Date: Apr. 22, 2020

(87) PCT Pub. No.: WO2019/081607
PCT Pub. Date: May 2, 2019

(65) Prior Publication Data
US 2020/0339986 A1   Oct. 29, 2020

(30) Foreign Application Priority Data
Oct. 24, 2017   (EP) .................................... 17306463

(51) Int. Cl.
*C12N 15/113*   (2010.01)
*C12Q 1/68*   (2018.01)

(52) U.S. Cl.
CPC ...... *C12N 15/113* (2013.01); *C12N 2310/113* (2013.01); *C12N 2310/141* (2013.01); *C12N 2310/3231* (2013.01); *C12N 2320/30* (2013.01)

(58) Field of Classification Search
None
See application file for complete search history.

(56) References Cited

U.S. PATENT DOCUMENTS

2017/0211074 A1    7/2017   Chen et al.
2017/0306326 A1*  10/2017   Amendt ................ C12N 15/111

OTHER PUBLICATIONS

International Search Report and Written Opinion dated Dec. 21, 2018 from International Application No. PCT/EP2018/079212 (Authorized Officer, Giovanni Macchia), 15 pages.
Fisher et al., "MicroRNA networks regulated by all-trans retinoic acid and Lapatinib control the growth, survival and motility of breast cancer cells", Oncotarget, 2015, vol. 6, No. 15, pp. 13176-13200.
Jayaraman et al., "Identification of novel diagnostic and prognostic miRNA signatures in endometrial cancer", Genes & Cancer, 2017, vol. 8, No. 5-6, pp. 566-576.
Huang et al., "miRNA-15a/16: as tumor suppressors and more", Future oncology, 2015, vol. 11, No. 16, pp. 2351-2363.
Li et al., "Epigenetic deregulation of miR-29a and miR-1256 by isoflavone contributes to the inhibition of prostate cancer cell growth and invasion", Epigenetics, 2012, vol. 7, No. 8, pp. 940-949.
Xu et al., "Decreased expression of MicroRNA-200 family in human breast cancer is associated with lymph node metastasis", Clinical and Translational Oncology, 2015, vol. 18, No. 3, pp. 283-288.
Kolacinska et al., "Association of microRNA-93, 190, 200b and Receptor Status in Core Biopsies from Stage III Breast Cancer Patients", DNA & Cell Biology, 2014, vol. 33, No. 9, pp. 624-629.
Chan et al., "Dual EGFR/HER2 Inhibition Sensitizes Prostate Cancer Cells to Androgen Withdrawal by Suppressing ErbB3", Clinical Cancer Research, 2011, vol. 17, No. 19, pp. 6218-6228.

* cited by examiner

*Primary Examiner* — Sean McGarry
(74) *Attorney, Agent, or Firm* — MH2 Technology Law Group LLP

(57) ABSTRACT

This invention relates to an agent that modulates the activity of a micro ribonucleic acid (miRNA), said miRNA being selected from the group consisting of miRNA 429-3p, miRNA 29c-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-5p and miRNA 542-5p, for use in the treatment of HER2-dependent cancer.

12 Claims, 27 Drawing Sheets
Specification includes a Sequence Listing.

MDA-MB231

```
                              SEQUENCE LISTING

<160> NUMBER OF SEQ ID NOS: 33

<210> SEQ ID NO 1
<211> LENGTH: 22
<212> TYPE: RNA
<213> ORGANISM: Homo sapiens

<400> SEQUENCE: 1
uaauacuguc ugguaaaacc gu                                              22

<210> SEQ ID NO 2
<211> LENGTH: 22
<212> TYPE: RNA
<213> ORGANISM: Homo sapiens

<400> SEQUENCE: 2
uagcaccauu ugaaaucggu ua                                              22

<210> SEQ ID NO 3
<211> LENGTH: 22
<212> TYPE: RNA
<213> ORGANISM: Homo sapiens

<400> SEQUENCE: 3
uagcaccauc ugaaaucggu ua                                              22

<210> SEQ ID NO 4
<211> LENGTH: 23
<212> TYPE: RNA
<213> ORGANISM: Homo sapiens

<400> SEQUENCE: 4
uagcaccauu ugaaaucagu guu                                             23

<210> SEQ ID NO 5
<211> LENGTH: 22
<212> TYPE: RNA
<213> ORGANISM: Homo sapiens

<400> SEQUENCE: 5
uaacacuguc ugguaacgau gu                                              22
```

```
<210> SEQ ID NO 6
<211> LENGTH: 22
<212> TYPE: RNA
<213> ORGANISM: Homo sapiens

<400> SEQUENCE: 6
uaauacugcc ugguaaugau ga                                              22

<210> SEQ ID NO 7
<211> LENGTH: 23
<212> TYPE: RNA
<213> ORGANISM: Homo sapiens

<400> SEQUENCE: 7
uaauacugcc ggguaaugau gga                                             23

<210> SEQ ID NO 8
<211> LENGTH: 22
<212> TYPE: RNA
<213> ORGANISM: Homo sapiens

<400> SEQUENCE: 8
uaacacuguc ugguaaagau gg                                              22

<210> SEQ ID NO 9
<211> LENGTH: 22
<212> TYPE: RNA
<213> ORGANISM: Homo sapiens

<400> SEQUENCE: 9
uagcagcaca uaaugguuug ug                                              22

<210> SEQ ID NO 10
<211> LENGTH: 22
<212> TYPE: RNA
<213> ORGANISM: Homo sapiens

<400> SEQUENCE: 10
uagcagcaca ucaugguuua ca                                              22

<210> SEQ ID NO 11
<211> LENGTH: 22
<212> TYPE: RNA
<213> ORGANISM: Homo sapiens

<400> SEQUENCE: 11
uagcagcacg uaaauauugg cg                                              22

<210> SEQ ID NO 12
<211> LENGTH: 22
<212> TYPE: RNA
<213> ORGANISM: Homo sapiens

<400> SEQUENCE: 12
cagcagcaau ucauguuuug aa                                              22

<210> SEQ ID NO 13
<211> LENGTH: 21
<212> TYPE: RNA
<213> ORGANISM: Homo sapiens

<400> SEQUENCE: 13
cagcagcaca cuguggluuug u                                              21
```

```
<210> SEQ ID NO 14
<211> LENGTH: 22
<212> TYPE: RNA
<213> ORGANISM: Homo sapiens

<400> SEQUENCE: 14
uccgagccug ggucucccuc uu                                              22

<210> SEQ ID NO 15
<211> LENGTH: 22
<212> TYPE: RNA
<213> ORGANISM: Homo sapiens

<400> SEQUENCE: 15
aaaccguuac cauuacugag uu                                              22

<210> SEQ ID NO 16
<211> LENGTH: 23
<212> TYPE: RNA
<213> ORGANISM: Homo sapiens

<400> SEQUENCE: 16
ucggggauca ucaugucacg aga                                             23

<210> SEQ ID NO 17
<211> LENGTH: 6
<212> TYPE: RNA
<213> ORGANISM: Artificial Sequence
<220> FEATURE:
<223> OTHER INFORMATION: Seed sequence of miRNA 200b-3p, miRNA 200c and
      miRNA 429

<400> SEQUENCE: 17 aauacu                                                                 6

<210> SEQ ID NO 18
<211> LENGTH: 6
<212> TYPE: RNA
<213> ORGANISM: Artificial Sequence
<220> FEATURE:
<223> OTHER INFORMATION: Seed sequence miRNA 200a-3p and miRNA 141-3p

<400> SEQUENCE: 18 aacacu                                                                 6

<210> SEQ ID NO 19
<211> LENGTH: 6
<212> TYPE: RNA
<213> ORGANISM: Artificial Sequence
<220> FEATURE:
<223> OTHER INFORMATION: Seed sequence miRNA 29a-3p, miRNA 29b-3p and
      miRNA 29c-3p

<400> SEQUENCE: 19 agcacc                                                                 6

<210> SEQ ID NO 20
<211> LENGTH: 7
<212> TYPE: RNA
<213> ORGANISM: Artificial Sequence
<220> FEATURE:
<223> OTHER INFORMATION: Seed sequence miRNA15a-5p, miRNA 15b-5p, miRNA
      16-5p, miRNA 424-5p and miRNA 497-5p

<400> SEQUENCE: 20
```

```
agcagca                                                             7

<210> SEQ ID NO 21
<211> LENGTH: 6
<212> TYPE: RNA
<213> ORGANISM: Artificial Sequence
<220> FEATURE:
<223> OTHER INFORMATION: Seed sequence miRNA 615-3p

<400> SEQUENCE: 21 ccgagc                                                              6

<210> SEQ ID NO 22
<211> LENGTH: 7
<212> TYPE: RNA
<213> ORGANISM: Artificial Sequence
<220> FEATURE:
<223> OTHER INFORMATION: Seed sequence miRNA 451a

<400> SEQUENCE: 22 aaccguu                                                             7

<210> SEQ ID NO 23
<211> LENGTH: 7
<212> TYPE: RNA
<213> ORGANISM: Artificial Sequence
<220> FEATURE:
<223> OTHER INFORMATION: Seed sequence miRNA 542-5p

<400> SEQUENCE: 23 cggggau                                                             7

<210> SEQ ID NO 24
<211> LENGTH: 27
<212> TYPE: DNA
<213> ORGANISM: Artificial Sequence
<220> FEATURE:
<223> OTHER INFORMATION: PCR primer (Forward MSN)

<400> SEQUENCE: 24
ggaatgagac aggacctagg atatctt                                      27

<210> SEQ ID NO 25
<211> LENGTH: 27
<212> TYPE: DNA
<213> ORGANISM: Artificial Sequence
<220> FEATURE:
<223> OTHER INFORMATION: PCR primer (Reverse MSN)

<400> SEQUENCE: 25
ggaatgagac aggacctagg atatctt                                      27

<210> SEQ ID NO 26
<211> LENGTH: 17
<212> TYPE: DNA
<213> ORGANISM: Artificial Sequence
<220> FEATURE:
<223> OTHER INFORMATION: PCR primer (Forward HER2)

<400> SEQUENCE: 26
gccgcagtga gcaccat                                                 17

<210> SEQ ID NO 27
<211> LENGTH: 19
<212> TYPE: DNA
```

```
<213> ORGANISM: Artificial Sequence
<220> FEATURE:
<223> OTHER INFORMATION: PCR Primer (Reverse HER2)

<400> SEQUENCE: 27
cgcagcttca tgtctgtgc                                                        19

<210> SEQ ID NO 28
<211> LENGTH: 21
<212> TYPE: DNA
<213> ORGANISM: Artificial Sequence
<220> FEATURE:
<223> OTHER INFORMATION: PCR primer (Forward GAPDH)

<400> SEQUENCE: 28
gatccctcca aaatcaagtg g                                                     21

<210> SEQ ID NO 29
<211> LENGTH: 22
<212> TYPE: DNA
<213> ORGANISM: Artificial Sequence
<220> FEATURE:
<223> OTHER INFORMATION: PCR Primer (Reverse GAPDH)

<400> SEQUENCE: 29
gcaaatgagc cccagccttc tc                                                    22

<210> SEQ ID NO 30
<211> LENGTH: 18
<212> TYPE: DNA
<213> ORGANISM: Artificial Sequence
<220> FEATURE:
<223> OTHER INFORMATION: miRNA 29c-3p inhibitor

<400> SEQUENCE: 30
ccgatttcaa atggtgct                                                         18

<210> SEQ ID NO 31
<211> LENGTH: 20
<212> TYPE: DNA
<213> ORGANISM: Artificial Sequence
<220> FEATURE:
<223> OTHER INFORMATION: miRNA 200b inhibitor

<400> SEQUENCE: 31
catcattacc aggcagtatt                                                       20

<210> SEQ ID NO 32
<211> LENGTH: 20
<212> TYPE: DNA
<213> ORGANISM: Artificial Sequence
<220> FEATURE:
<223> OTHER INFORMATION: miRNA 429-3p inhibitor

<400> SEQUENCE: 32
cggttttacc agacagtatt                                                       20

<210> SEQ ID NO 33
<211> LENGTH: 19
<212> TYPE: DNA
```

```
<213> ORGANISM: Artificial Sequence
<220> FEATURE:
<223> OTHER INFORMATION: control miRNA inhibitor

<400> SEQUENCE: 33
taacacgtct atacgccca                                              19
```

TREATMENT OF HER-2 DEPENDENT CANCER USING AN AGENT THAT MODULATES THE ACTIVITY OF A MIRNA

CROSS-REFERENCE TO RELATED APPLICATIONS

This application is a U.S. National Stage Application of International Application No. PCT/EP2018/079212, filed on Oct. 24, 2018, which claims priority to European Patent Application No. 17306463.5, filed on Oct. 24, 2017, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 22, 2020, is named 1H316870_0005_ST25_PCT2.txt and is 7 kilobytes in size.

BACKGROUND OF THE INVENTION

Breast cancer is the most common cancer in women worldwide, with nearly 1.7 million new cases diagnosed in 2012 (second most common cancer overall). This represents about 12% of all new cancer cases and 25% of all cancers in women. About half the breast cancer cases and 60% of the deaths are estimated to occur in economically developing countries. The rate of incidence observed in France is among the strongest in Europe and is in constant increase.

About 20 to 30% of primary human breast cancers are due to the deregulated expression of HER2: it represents approximately 8,000 patients a year in France and 450,000 patients a year worldwide. HER2 is a well-known member of the human epidermal growth factor receptor (HER/EGFR/ERBB) family. Only 25% of the treated patients respond to the actual therapies. The actual strategies aiming at targeting the extracellular domain of HER2 (anti-HER2 antibody therapies such as Herceptin/Trastuzumab, Pertuzumab and the recently developed Trastuzumab emtansine from Genentech, USA) or the kinase activity of the receptor (small molecule tyrosine kinase inhibitors, such as Lapatinib/Tykerb, GSK, USA) have proven to exhibit limited actions.

In particular, these molecules have no potent action on the mutated and truncated forms of HER2. Concerning Trastuzumab, 66% to 88% of treated patients never respond to treatment (i.e. present a "primary resistance") and among the one-third of the treated patients that respond to this agent, a disease progression on average in less than one year (i.e. develop an "acquired resistance") is generally observed. The efficacy is limited by the development of therapeutic resistance mainly attributed to the expression of p95HER-2, as this highly active truncated form of HER2 lacks the recognition site for Trastuzumab.

Treatments with small molecule tyrosine kinase inhibitors (Lapatinib) are often associated to increase toxicity due to a non-specific inhibition of promiscuous ErbB and non-ErbB kinases by these agents, limiting the extent to which they can be used safely. The median duration of response to lapatinib was less than one year, and a majority of Trastuzumab-pretreated patients (~80%) failed to respond.

There is therefore a need for developing new methods for treating HER2-dependent cancer, such as HER2+ breast cancer. In particular, there is an urgent need for the development of alternative approaches for the treatment of HER2-dependent cancer with a reduced risk of toxicity.

The Applicant has identified new targets, micro ribonucleic acids (miRNAs), which constitute a new approach for the treatment of HER2-dependent cancers.

SUMMARY OF THE INVENTION

The inventors therefore propose here to modulate the activity of specific miRNAs to treat HER2-dependent cancers.

The inventors have identified miRNAs that regulate HER2 expression and/or activation. In particular, certain miRNAs (e.g. miRNA 429-3p, miR29c-3p and miR200b-3p) are able to reduce HER2 activation. These miRNAs constitute therefore a new therapeutic approach to decrease HER2 aberrant activation in HER2-dependent cancer, such as HER2+ breast cancers. Such compounds inhibit HER2 activation by a mechanism which differs from the one of known therapies, such as Trastuzumab and Lapatinib and can be used to efficiently block the activation of Trastuzumab-resistant cell lines.

The invention relates to an agent that modulates the activity of a micro ribonucleic acid (miRNA), said miRNA being selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-5p and miRNA 542-5p, for use in the treatment of HER2-dependent cancer.

DETAILED DESCRIPTION OF THE INVENTION

Definitions

The term "HER2", as used herein, refers to "Human Epidermal growth factor Receptor 2" which is a protein member of the human epidermal growth factor receptor family. "HER2" is also frequently called "ErbB2". "ErbB2" and "HER2" are used interchangeably in the present invention.

The term "HER2-dependent cancer" or "HER2 positive cancer" or "HER2+ cancer", as used herein, refers to cancer involving exacerbated HER2 activation. In particular, the term "HER2-dependent cancer" refers to any cancer case for which cancer cells exhibiting a deregulation of HER2 gene have been identified, in opposition to "HER2-independent cancer" or "HER2 negative cancer" or "HER2− cancer". More particularly said deregulation can correspond to an amplification of HER2 gene. This amplification can be detected at the genetic level, or at the protein level. For example, guidelines emitted by the American society of Clinical Oncology/College of American Pathologists (ASCO/CAP) for breast cancer set several cut-offs for determining the ErbB2 status of breast cancer. These guidelines prescribe that a cancer should be considered as "HER2-dependent" if, for the primary site and if possible for the metastatic site:

a uniform and intense membrane staining of more than 30
  ° A) of invasive tumor cells is observed in immunochemistry (IHC), or
i) a FISH amplified ratio of HER2 to CEP17 (chromosome 17 centromere) superior or equal to 2 (dual probe testing) or ii) a FISH amplified ratio of HER2 to CEP17 (chromosome 17 centromere) inferior to 2 (dual probe testing) with an average HER2 copy number of at least 6 copies per nucleus (single probe testing) is determined, or iii) a single probe average of at least 6 signals for the HER2 copy number per cells.

Besides, a cancer is considered as "HER2-independent" when, for the primary site and if possible for the metastatic site:
  in IHC, no staining or a weak incomplete membrane staining, or a weak but complete membrane staining is observed in less than 10% of cells, or
  the FISH HER2/CEP17 ratio inferior to 2 with an average copy number of HER2 inferior to 4 signals per cells is noticed (dual probe testing), or an average copy number of HER2 inferior to 4 signals per cell is noticed (in cases where a single probe is used).

The HER2 status will be considered as equivocal (then a new test should be performed) when, for the primary site and, if possible, for the metastatic site:
  in IHC, i) an incomplete labelling of circumferential membrane and/or weak/moderate labelling is noticed but within superior to 10% of the invasive tumor cells or ii) a complete and intense labelling of circumferential membrane is noticed but for 10% or less of the invasive tumor cells, or
  the FISH HER2/CEP17 ratio inferior to 2 with an average copy number of HER2 of at least 4 signals but less than 6 signals per cell is noticed (dual probe testing), or an average copy number of HER2 of at least 4 signals but less than 6 signals per cell is noticed (in cases where a single probe is used).

Deregulation of HER2 gene can also correspond to activating mutations in HER2 gene disregarding its copy number, leading to an increase of the tyrosine kinase activity of HER2. For example, said activating mutations can be V659E, G309A, D769H, D769Y, V777L, P780ins, V842I, R896C, K753E or L755S and can be detected by Polymerase Chain Reaction or any sequencing technique [Bose et al. Cancer Discov. 2013, 3(2), 224-237; Zuo et al. Clin Cancer Res 2016, 22(19), 4859-4869]. Also, both an amplification of HER2 gene and a somatic activating mutation can be detected in the same case of cancer.

Well known molecular biology tests other than Fish or IHC, using negative and positive control cells with an established HER2 status, can be used for determining the HER2 status of a cancer by way of comparison, as for example Enzyme-Linked Immunosorbent Assays, Western blotting assays, Polymerase Chain Reaction, etc.

Preferably, the HER2-dependent cancer according to the invention is selected from the group consisting of breast cancer, female genital tract cancer, such as endometrial cancer, uterine cancer or ovarian cancer, bladder cancer, anal cancer, colorectal cancer, in particular uterine serous cancer, such as uterine papillary serous carcinoma, lung cancer, in particular non-small-cell lung cancer, liver cancer, kidney cancer, gastroesophageal cancer, stomach cancer, pancreas cancer and gastric cancer. In a preferred embodiment, the HER2-dependent cancer may be HER2+ breast cancer, HER2+ ovarian cancer, HER2+ bladder cancer, HER2+ colorectal cancer, HER2+ uterine papillary serous carcinoma and HER2+ gastric cancer, preferably HER2+ breast cancer.

The HER2+ breast cancer according to the invention may be Moesin negative. The term "Moesin negative" means the expression of Moesin is reduced compared to healthy patients. In patients (data from survival analysis server) the cutoff is 2176 (relative value from gene expression). Accordingly, patients with gene expression from 390 to 2176 are "MSN negative" (or MSN low), and patients with gene expression from 2176 to 12965 are "MSN positive" (or MSN high). For example, when MSN expression on HER2+ breast cancer cells is less than 11% of the MSN expression on normal epithelial cells (HMEC), HER2+ breast cancer is considered as "MSN negative".

The term "agent", as used herein, is used in the broadest sense, and includes an oligonucleotide, a chemical, a polypeptide or a combination thereof.

The term "oligonucleotide" in the context of the present invention, refers to a molecule formed by covalent linkage of two or more nucleotides. It will be recognized that when referring to a sequence of the oligonucleotide, what is referred to is the sequence of bases, such as A, T, G, C or U. The oligonucleotide may consist of or comprise a contiguous nucleotide sequence of at least 8 nucleotides, for example from 8 to 30 nucleotides, preferably 22±2.

The term "micro ribonucleic acid" or "miRNA", as used herein, refers to a small non-coding RNA molecule (generally containing about 18-25 nucleotides) found in plants, animals and some viruses, that functions in RNA silencing and post-transcriptional regulation of gene expression. The miRNA according to the invention may be located within the cell or may be located in the extracellular environment. The latter are generally known as circulating miRNA or extracellular miRNA.

The term "anti-miRNA", as used herein, is used in the broadest sense, and includes any agent that partially or fully suppresses, inhibits, or neutralizes a miRNA. Methods for identifying an anti-miRNA can comprise contacting a miRNA with a candidate anti-miRNA and measuring the specific binding to and/or inhibition (in vivo or in vitro) of the miRNA. The anti-miRNA of the invention may be an antisense compound, such as an antisense oligonucleotide. The anti-miRNA of the invention may also be a miRNA sponge, which is well known in the art for its capability to sequester a miRNA.

The term "antisense compound", as used herein, means a compound comprising or consisting of an oligonucleoside, preferably an oligonucleotide, at least a portion of which is complementary to a target nucleic acid to which it is capable of hybridizing, resulting in at least one antisense activity. The antisense compound is called "antisense oligonucleotide" when it consists essentially of nucleotides.

The term "antisense oligonucleotide", as used herein, means an oligonucleotide which consists or comprises of a contiguous nucleotides sequence which is fully complementary to, or essentially complementary to (i.e. may comprise one or two mismatches), to a miRNA sequence, or a corresponding subsequence thereof. In some embodiments, "antisense oligonucleotide" means a single-stranded RNA molecule designed to specifically bind to and inhibit a miRNA and enable miRNA down-regulation of said miRNA activity.

The antisense oligonucleotide may be chemically modified (e.g. may comprise one or more nucleotide analogues).

The term "nucleotide analogues", in the context of the present invention, refers to variants of natural nucleotides, such as DNA or RNA nucleotides, by virtue of modifications in the sugar and/or base moieties. Analogues could in principle be merely "silent" or "equivalent" to the natural nucleotides in the context of the antisense compound or the miRNA mimic, i.e. have no functional effect on the way the oligonucleotide works to hybridize miRNA. Such "equivalent" analogues may nevertheless be useful if, for example, they are easier or cheaper to manufacture, or are more stable to storage or manufacturing conditions, or represent a tag or label. Preferably, however, the nucleotide analogues will have a functional effect on the way in which the antisense compound works to hybridize miRNA; for example by producing increased binding affinity to the miRNA and/or increased resistance to nucleases and/or increased ease of transport into the cell. The nucleotide analogues may also have a functional effect on the way in which the miRNA mimic increased resistance to nucleases and/or increased ease of transport into the cell. In some embodiments, a nucleotide analogue is a locked nucleic acids (LNA) nucleotide.

The terms "complementarity" and "homology", as used herein, are interchangeable and mean the percentage identity (or percentage homology) between the nucleotides sequence of the antisense compound and the sequence of the miRNA. For example, the percentage of complementarity (or homology) may be calculated by counting the number of aligned bases that are identical between the 2 sequences, dividing by the total number of contiguous nucleotides, and multiplying by 100.

The term "miRNA mimic", as used herein, means a RNA, such as a single-stranded RNA, a double-stranded RNA or a hairpin RNA, that mimic a miRNA and that enable up-regulation of said miRNA activity. The miRNA mimic may be chemically modified (e.g. may comprise one or more nucleotide analogues).

The term "modulate the activity", as used herein, is used in the broadest sense, and includes "decrease the activity" and "increase the activity". The term "decrease the activity", as used herein, means partially or fully suppress, inhibit, or neutralize the activity of a miRNA. The term "increase the activity", as used herein, means partially or fully increase, activate, mimic, up-regulate or stimulate the activity of a miRNA.

The term "patient" or "individual", as used herein, refers to a human or non-human mammal (such as a rodent (mouse, rat), a feline, a canine, or a primate) affected or likely to be affected with cancer. Preferably, the subject is a human, man or woman.

The term "treating" or "treatment" means reversing, alleviating, inhibiting the progress of, or preventing the disorder or condition to which such term applies, or one or more symptoms of such disorder or condition. In particular, the treatment of the disorder may consist in destroying, depleting or inhibiting the proliferation of cancer cells. Most preferably, such treatment leads to the complete depletion of cancer cells.

Modulated miRNA

The invention relates to an agent that modulates the activity of a micro ribonucleic acid (miRNA), said miRNA being selected from the group consisting of miRNA 429-3p, miRNA 29c-3p, miRNA 29a-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-5p and miRNA 542-5p, for use in the treatment of HER2-dependent cancer.

In some embodiments, said miRNA is a human miRNA as detailed in Table

TABLE 1 modulated miRNA of the invention

| miRNA | Detailed name | Nucleotide sequence | Reference (miRBase) | SEQ ID NO |
|---|---|---|---|---|
| miRNA-429-3p | hsa-miRNA-429-3p | uaauacugucugguaaaaccgu | MIMAT0001536 | 1 |
| miRNA 29c-3p | hsa-miRNA 29c-3p | uagcaccauuugaaaucgguua | MIMAT0000681 | 2 |
| miRNA 29a-3p | hsa-miRNA 29a-3p | uagcaccaucugaaaucgguua | MIMAT0000086 | 3 |
| miRNA 29b-3p | hsa-miRNA 29b1-3p hsa-miRNA 29b2-3p | uagcaccauuugaaaucaguguu | MIMAT0000100 | 4 |
| miRNA 200a-3p | hsa-miRNA-200a-3p | uaacacugucugguaacgaugu | MIMAT0000682 | 5 |
| miRNA 200b-3p | hsa-miRNA-200b-3p | uaauacugccugguaaugauga | MIMAT0000318 | 6 |
| miRNA 200c-3p | hsa-miRNA-200c-3p | uaauacugccggguaaugaugga | MIMAT0000617 | 7 |
| miRNA 141-3p | hsa-miRNA-141-3p | uaacacugucugguaaagaugg | MIMAT0000432 | 8 |
| miRNA 15a-5p | hsa-miRNA 15a-5p | uagcagcacauaaugguuugug | MIMAT0000068 | 9 |
| miRNA 15b-5p | hsa-miRNA 15b-5p | uagcagcacaucaugguuuaca | MIMAT0000417 | 10 |
| miRNA 16-5p | hsa-miRNA 16-5p | uagcagcacguaaauauuggcg | MIMAT0000069 | 11 |
| miRNA 424-5p | hsa-miRNA-424-5p | cagcagcaauucauguuuugaa | MIMAT0001341 | 12 |
| miRNA 497-5p | hsa-miRNA-497-5p | cagcagcacacuguggunugu | MIMAT0002820 | 13 |
| miRNA 615-3p | hsa-miRNA-615-3p | uccgagccuggguccucuu | MIMAT0003283 | 14 |
| miRNA 451a-5p | hsa-miRNA-451a | aaaccguuaccauuacugaguu | MIMAT0001631 | 15 |
| miRNA 542-5p | hsa-miRNA-542-5p | ucggggaucaucaugucacgaga | MIMAT0003340 | 16 |

In some embodiments, the agent is an anti-miRNA or a miRNA mimic.

Anti-miRNA

The agent for use according to the invention may be an anti-miRNA. Preferably, the agent is an anti-miRNA selected from the group consisting of anti-miRNA 429-3p, anti-miRNA 29c-3p, anti-miRNA 200a-3p, anti-miRNA 200b-3p, anti-miRNA 200c-3p, anti-miRNA 497-5p, anti-miRNA 615-3p, anti-miRNA 451a-5p and anti-miRNA 542-5p, anti-miRNA 15a-5p, anti-miRNA 16-5p and anti-miRNA 424-5p.

In particular, said anti-miRNA is an antisense compound (also called "antagomiR") which targets the miRNA, preferably the miRNA selected from the group consisting of anti-miRNA 429-3p, anti-miRNA 29c-3p, anti-miRNA 200a-3p, anti-miRNA 200b-3p, anti-miRNA 200c-3p, anti-miRNA 497-5p, anti-miRNA 615-3p, anti-miRNA 451a and anti-miRNA 542-5p, anti-miRNA 15a-5p, anti-miRNA 16-5p and anti-miRNA 424-5p. In particular, said antisense compound comprises a contiguous nucleotides sequence, e.g. at least 8 contiguous nucleotides, complementary to a corresponding sequence of the miRNA, for example from 8 to 30 nucleotides.

In some embodiments, said antisense compound comprises at least a contiguous nucleotides sequence complementary to the seed sequence of the miRNA. The seed sequence of a miRNA is essential for the binding of said miRNA to its target mRNA. A skilled person can easily determine the seed sequence of a miRNA. Examples of seed sequences are:

```
Seed sequence of miRNA 200b-3p, miRNA 200c and
miRNA 429-3p:
                                    (SEQ ID NO: 17)
aauacu Seed sequence miRNA 200a-3p and miRNA 141-3p:
                                    (SEQ ID NO: 18)
aacacu Seed sequence miRNA 29a-3p, miRNA 29b-3p and
miRNA 29c-3p:
                                    (SEQ ID NO: 19)
agcacc Seed sequence nniRNA15a-5p, miRNA 15b-5p, miRNA
16-5p, miRNA 424-5p and miRNA 497-5p:
                                    (SEQ ID NO: 20)
agcagca Seed sequence miRNA 615-3p:
                                    (SEQ ID NO: 21)
ccgagc Seed sequence mRNA 451a-5p:
                                    (SEQ ID NO: 22)
aaccguu Seed sequence miRNA 542-5p:
                                    (SEQ ID NO: 23)
cggggau
```

In some embodiments, the antisense compound comprises a contiguous nucleotides sequence complementary to at least 50% of the miRNA, preferably at least 60%, 70%, 80%, 90%, for example 95%, 96%, 97%, 98%, 99% of the miRNA.

In some embodiments, the antisense compound comprises a contiguous nucleotides sequence complementary to the full-length mi-RNA (i.e. complementary to 100% of the miRNA).

In some embodiments, the antisense compound targeting a miRNA is complementary to a corresponding sequence of the miRNA across the length of the antisense compound and in some embodiments the 3' nucleotide of the antisense compound is complementary to (i.e. aligns to) the first, second, third or fourth 5' nucleotides of the miRNA.

Examples of commercialized antisense compounds are listed in Table 2.

TABLE 2 commercialized antisense compounds

| Targeted miRNA | Commercial reference (provider) |
| --- | --- |
| miRNA 429-3p | INH0388 (Active motif) |
| miRNA 29c-3p | INH0080 (Active motif) |
| miRNA 15a-5p | INH0027 (Active motif) |
| miRNA 16-5p | INH0035 (Active motif) |
| miRNA 200a-3p | INH0250 (Active motif) |
| miRNA 200b-3p | INH0252 (Active motif) |
| miRNA 200c-3p | INH0251 (Active motif) |
| miRNA 424-5p | INH0385 (Active motif) |
| miRNA 497-5p | INH0430 (Active motif) |
| miRNA 615-3p | INH0609 (Active motif) |
| miRNA 451a-5p | INH0399 (Active motif) |
| miRNA 542-5p | INH0509 (Active motif) |

In a preferred embodiment, said anti-miRNA is an antisense compound chemically modified, for example to increase its stability, e.g. with respect to nucleases, and/or its cellular uptake.

Numerous chemical modifications of antisense compounds have been suggested, and typically antisense oligonucleotides for therapeutic use, such as the contiguous nucleotide sequence thereof comprise one or more nucleotide analogues.

In some embodiments, the invention relates to an antisense compound comprising nucleotide analogues. In a preferred embodiment, at least 20%, preferably at least 40%, at least 50%, at least 60%, at least 70% or at least 80%, for example a least 90% or 100%, of the nucleotides of the antisense compound are nucleotide analogues.

In a preferred embodiment, the nucleotide analogues are locked nucleic acids (LNA) nucleotides. In a preferred embodiment, at least 20%, preferably at least 40%, at least 50%, at least 60%, at least 70% or at least 80%, for example a least 90% or 100%, of the nucleotides of the antisense compound are LNA nucleotides. Thus, the antisense compound may be called a "LNA antisense oligonucleotide" when 100% of the nucleotides of the antisense compound are LNA nucleotides. In some embodiments, the locked nucleic acids (LNA) nucleotides are LNA anti-miRNA 29c-3p, LNA anti-miRNA 200b-3p or LNA anti-miRNA 429-3p, for example SEQ ID NO: 30, SEQ ID NO: 31 or SEQ ID NO: 32 respectively.

miRNA Mimic

The agent for use according to the invention may be a miRNA mimic. The miRNA mimic has the cellular function of the miRNA and enables up-regulation of said miRNA activity.

In a preferred embodiment, the miRNA mimic is selected from the group consisting of miRNA 29b-3p mimic and miRNA 15b-5p mimic. This means that the miRNA mimic has the cellular function of miRNA 29b-3p or miRNA 15b-5p, for example the miRNA mimic sequence comprise has at least 90% homology, such as 95%, 96%, 97%, 98%, 99% or 100% homology with the nucleotide sequence of miRNA 29b-3p and miRNA 15b-5p.

In a preferred embodiment, said miRNA mimic is chemically modified, for example to increase its stability, e.g. with respect to nucleases, and/or its cellular uptake.

Accordingly, in a preferred embodiment, the miRNA mimic comprises nucleotide analogues. Preferably, at least 20%, preferably at least 40%, at least 50%, at least 60%, at least 70% or at least 80%, for example a least 90% or 100%, of the nucleotides of the miRNA mimic are nucleotide analogues.

In some embodiments, the nucleotide analogues are locked nucleic acids (LNA) nucleotides. In a preferred embodiment, at least 20%, preferably at least 40%, at least 50%, at least 60%, at least 70% or at least 80%, for example a least 90% or 100%, of the nucleotides of the miRNA mimic are LNA nucleotides.

In a preferred embodiment, the nucleotide analogues are 2'-F/MOE nucleotides. In a preferred embodiment, at least 20%, preferably at least 40%, at least 50%, at least 60%, at least 70% or at least 80%, for example a least 90% or 100%, of the nucleotides of the miRNA mimic are 2'-F/MOE nucleotides.

The nucleotide analogues, such as 2'-F/MOE nucleotides, is particularly advantageous when they provide a functional effect on the way in which the miRNA mimic has increased resistance to nucleases and/or increased ease of transport into the cell.

HER2-Dependent Cancer

In some embodiments, the HER2-dependent cancer is selected from the group consisting breast cancer, female genital tract cancer, such as endometrial cancer, uterine cancer or ovarian cancer, bladder cancer, anal cancer, colorectal cancer, in particular uterine serous cancer, such as uterine papillary serous carcinoma, lung cancer, in particular non-small-cell lung cancer, liver cancer, kidney cancer, gastroesophageal cancer, stomach cancer, pancreas cancer and gastric cancer. In a preferred embodiment, the HER2-dependent cancer may be HER2+ breast cancer, HER2+ ovarian cancer, HER2+ bladder cancer, HER2+ colorectal cancer, HER2+ uterine papillary serous carcinoma and HER2+ gastric cancer, preferably HER2+ breast cancer. The breast cancer may be Moesin negative.

Pharmaceutical Composition

The agent of the invention may be used in a pharmaceutical composition. Suitably, such composition comprises a pharmaceutically acceptable diluent, carrier, salt or adjuvant.

Carriers or diluents useful in the pharmaceutical composition may include, but are not limited to saline, buffered saline, dextrose, water, glycerol, ethanol and combinations thereof. The agent formulated as a pharmaceutical composition may be administered in any effective, convenient manner effective for having a therapeutic effect including, for example, administration by oral, intravenous, intramuscular, intradermal, intranasal, topical routes among others. In some embodiments, the agent may be administered directly to a tumour or may be targeted to the tumour via systemic administration.

Combination Treatments

In some embodiments, the agent of the invention is for use in a combination treatment with another therapeutic agent. In some embodiments, another therapeutic agent is a therapeutic agent known for treating HER2+ breast cancer. For example, the antitumoral treatment may aim at targeting the extracellular domain of HER2, such as anti-HER2 antibody therapies, for example Herceptin/Trastuzumab, Pertuzumab and Trastuzumab emtansine (Genentech, USA); or the antitumoral treatment may aim at targeting the kinase activity of HER2, such as small molecule tyrosine kinase inhibitors, for example Lapatinib/Tykerb (GSK, USA). The antitumoral treatment may also be a taxane-based chemotherapy, such as paclitaxel.

In some embodiments, the agent of the invention is for use in first line therapy to provide alternative treatment combinations to maximize the clinical benefit from Trastuzumab (and consequently reduce the doses of Trastuzumab required and its associated toxicity) and/or in second line therapy to prevent or delay resistance to Trastuzumab.

MSN$^{hi}$ means high expression of MSN.

MSN$^{lo}$ means low expression of MSN.

FIGS. 2A-2F represent the survival analyses of patients with HER2+ breast cancer (HER2+ BC) or HER2− breast cancer (HER2− BC) depending on miRNA 29 family level of expression (miRNA 29a-3p, miRNA 29b-3p and miRNA 29c-3p). BC means Breast Cancer.

FIGS. 3A-3J represent the survival analyses of patients with HER2+ breast cancer (HER2+ BC) or HER2− breast cancer (HER2− BC) depending on miRNA 200 family level of expression (miRNA 200a-3p, miRNA 200b-3p, miRNA 200c-3p, miRNA 141-3p and miRNA 429-3p). BC means Breast Cancer.

FIGS. 4A-4L represent the survival analyses of patients with HER2+ breast cancer (HER2+ BC) or HER2− breast cancer (HER2− BC) depending on miRNA 15 family level of expression (miRNA 15a-5p, miRNA 15b-5p, miRNA 16-5p, miRNA 195-5p, miRNA 424-5p and miRNA 497-5p). BC means Breast Cancer.

FIGS. 5A-5F represent the survival analyses of patients with HER2+ breast cancer ((HER2+ BC) or HER2− breast cancer (HER2− BC) depending on miRNA 615-3p, miRNA 451a-5p and miRNA 542-5p level of expression. BC means Breast Cancer.

Figure 6A:
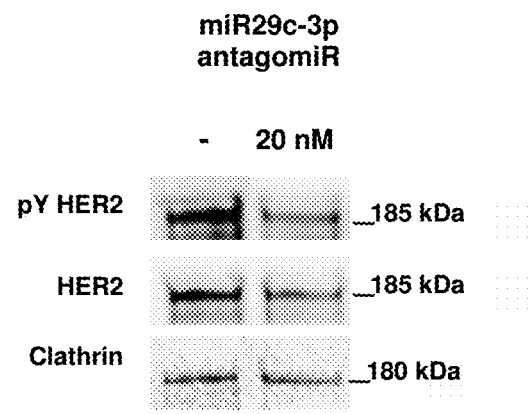
Figure 6B:
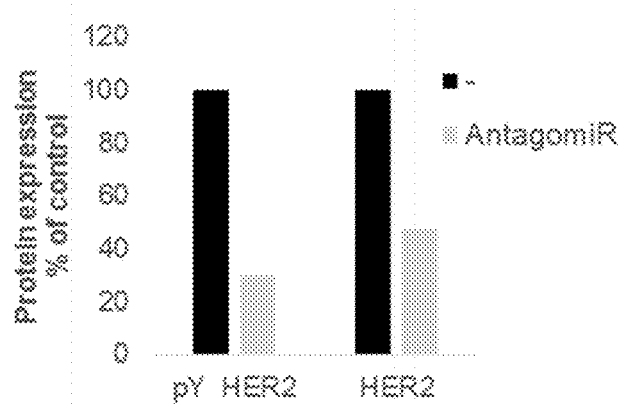

FIGS. 6A-6B represent the effect of 20 nM anti-miRNA 29c-3p (antagomiR) transfected 48 h in SKBR3, a HER2+ breast cancer cell line, on HER2 activation (pYHER2) and expression (HER2) as well as on Moesin (MSN) and Clathrin level of expression analyzed by western blot.

Figure 7A:
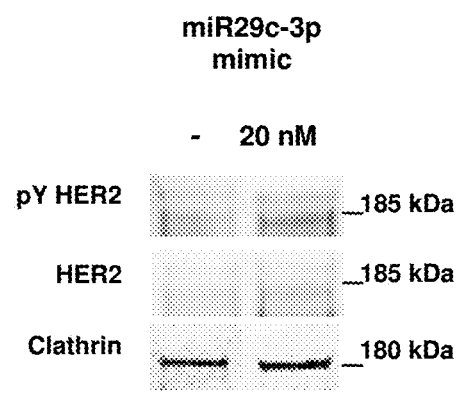
Figure 7B:
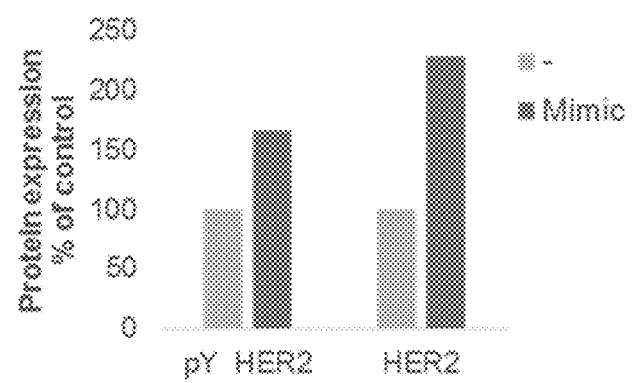

FIGS. 7A-7B represent the effect of 20 nM miRNA 29c-3p mimic transfected 48 h in MDAMB231, a HER2− breast cancer cell line, on HER2 activation (pYHER2) and expression (HER2) as well as on Moesin (MSN) and Clathrin level of expression analyzed by western blot.

Figure 8:
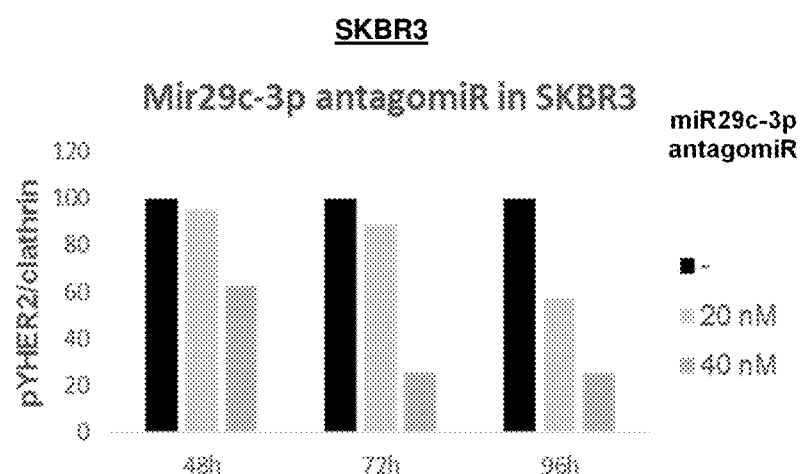

FIG. 8 represents the quantification of the effect of 20 and 40 nM anti-miRNA 29c-3p (antagomiR) transfected 72 h or 96 h in SKBR3, a HER2+ breast cancer cell line, on HER2 activation (pYHER2/Clathrin) analyzed by western blot.

Figure 9:
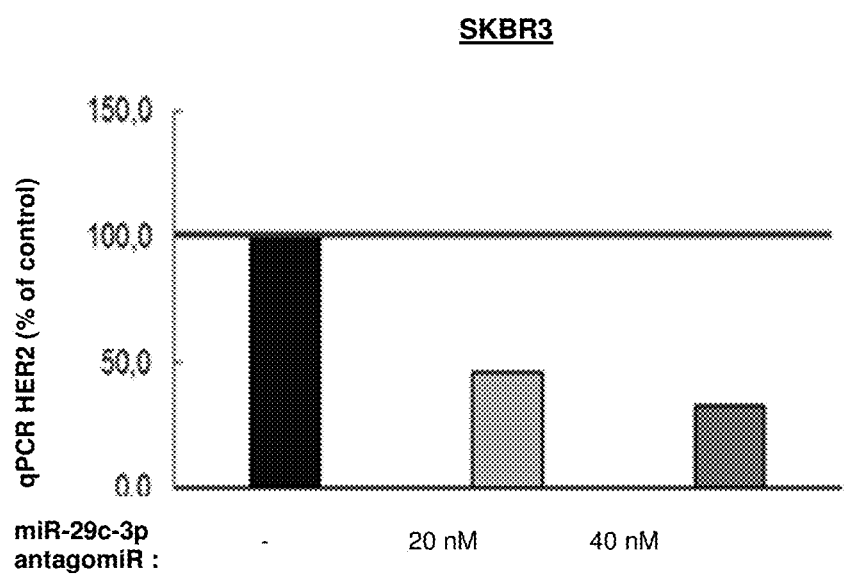

FIG. 9 represents the effect of 20 and 40 nM anti-miRNA 29c-3p (antagomiR) transfected 72 h in SKBR3, a HER2+ breast cancer cell line, on HER2 mRNA expression level analyzed by qRT-PCR.

Figure 10A:
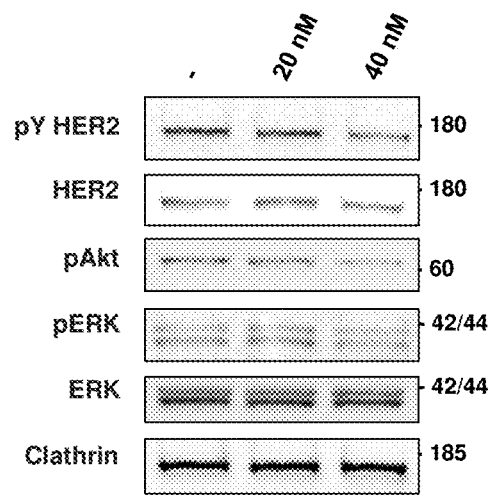
Figure 10B:
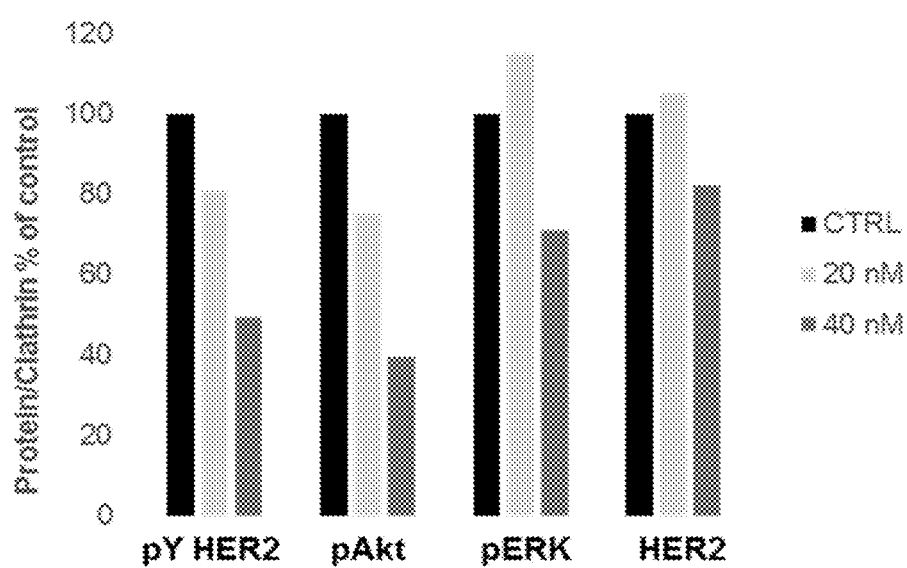

FIGS. 10A-10B represent the effect of 20 and 40 nM anti-miRNA 29c-3p (antagomiR) transfected 72 h in BT474, a HER2+ breast cancer cell line, on HER2 activation (pYHER2) and expression (HER2) as well as on activation of Akt (pAkt) and ERK (pERK) and on Clathrin level of expression analyzed by western blot.

Figure 11:
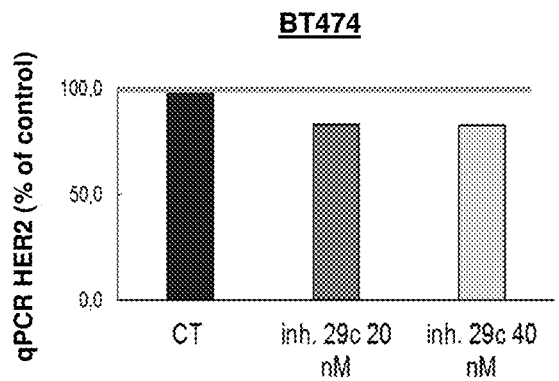

FIG. 11 represents the effect of 20 and 40 nM anti-miRNA 29c-3p (inh 29c) transfected 72 h in BT474, a HER2+ breast cancer cell line, on HER2 mARN expression level analyzed by qRT-PCR. CT means "Control"; inh. 29c means anti-miRNA 29c-3p).

Figure 12A:
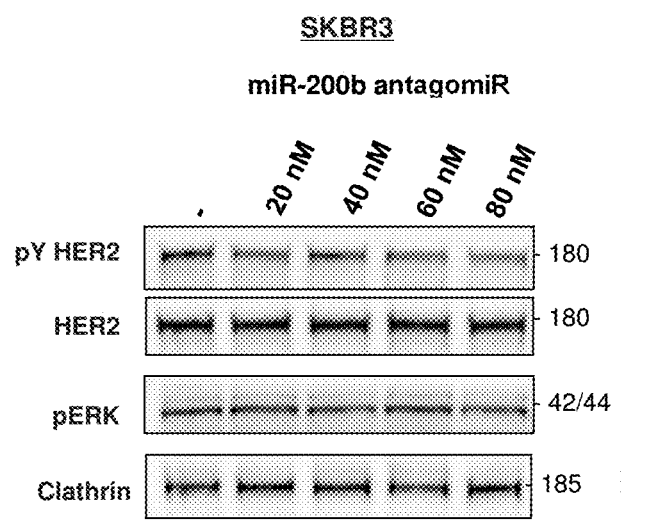
Figure 12B:
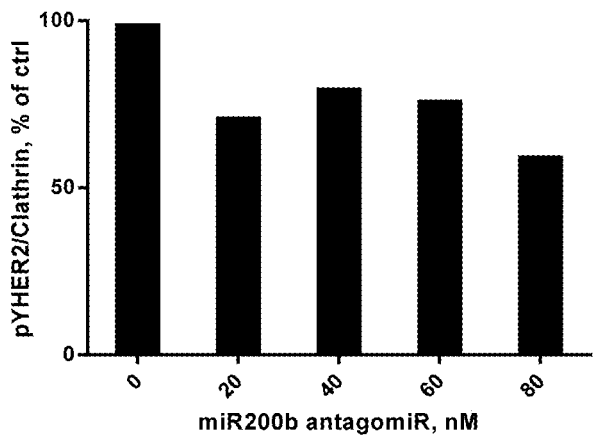

FIGS. 12A-12B represent the effect of 20, 40, 60 and 80 nM anti-miRNA 200b-3p (antagomiR) transfected 72 h in SKBR3, a HER2+ breast cancer cell line, on HER2 activation (pYHER2) and expression (HER2), on Moesin (MSN) expression as well as on the activation of ERK (pERK) and on Clathrin level of expression analyzed by western blot.

Figure 13A:
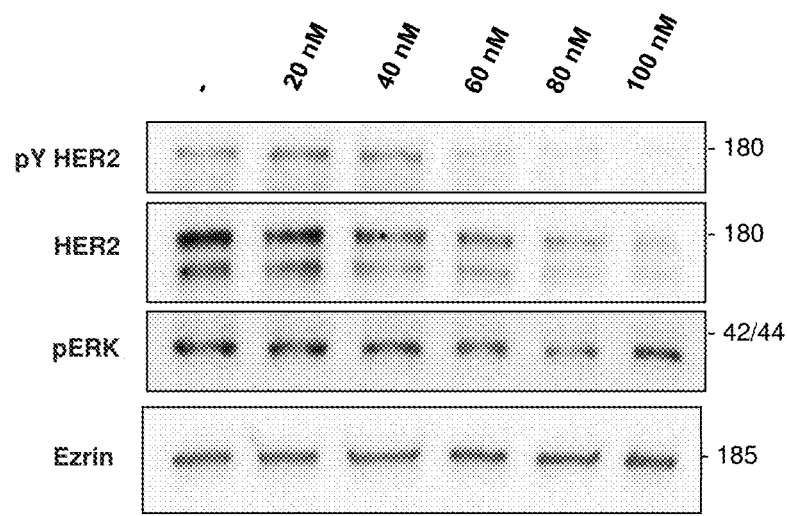
Figure 13B:
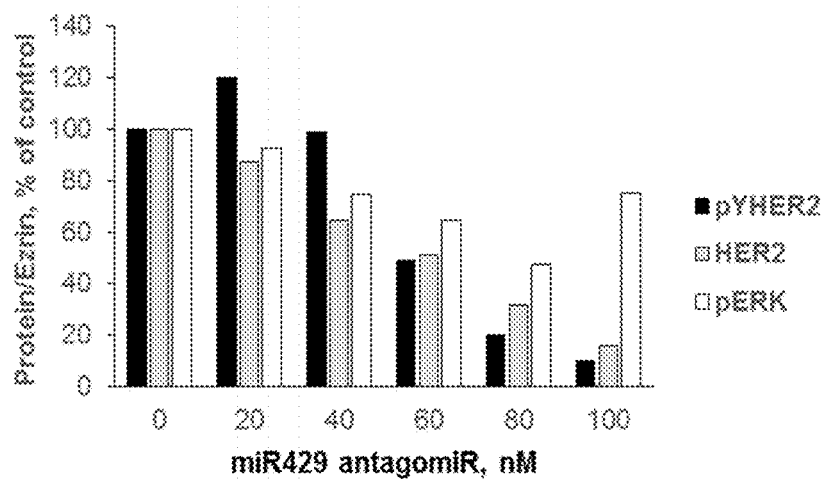

FIGS. 13A-13B represent the effect of 20, 40, 60, 80 and 100 nM anti-miRNA 429-3p (antagomiR) transfected 72 h in SKBR3, a HER2+ breast cancer cell line, on HER2 activation (pYHER2) and expression (HER2), on Moesin (MSN) expression as well as on the activation of ERK (pERK) and on Ezrin level of expression analyzed by western blot.

Figure 14:
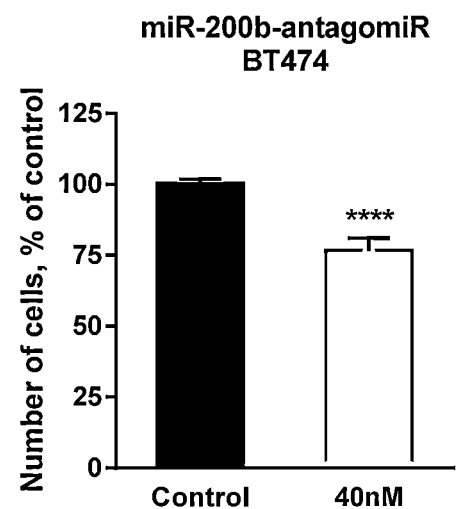

FIG. 14 represents the effect of 40 nM anti-miRNA 200b-3p (antagomiR) transfected 96 h in BT474, a HER2+ breast cancer cell line, on HER2-dependent proliferation analyzed by MTT assay.

Figure 15:
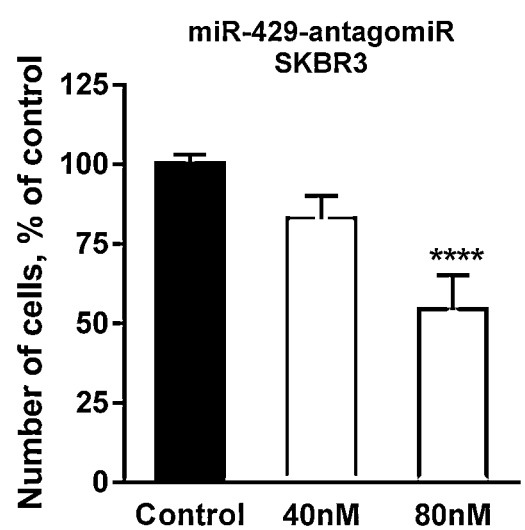

FIG. 15 represents the effect of 40 and 80 nM anti-miRNA 429-3p (antagomiR) transfected 96 h in SKBR3, a HER2+ breast cancer cell line, on HER2-dependent proliferation analyzed by MTT assay.

Figure 16:
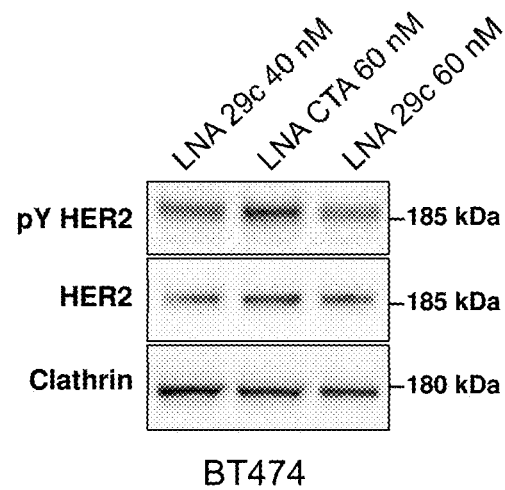

FIG. 16 represents the effect of 40 and 60 nM LNA anti-miRNA 29c-3p (LNA 29c) or of 60 nM control anti-miRNA LNA (LNA CTA) transfected 72 h in BT474, a HER2+ breast cancer cell line, on HER2 activation (pYHER2) and expression (HER2), and on Clathrin level of expression analyzed by western blot.

Figure 17:
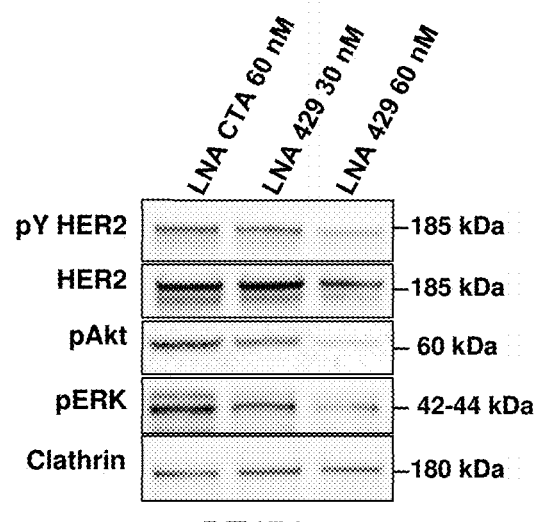

FIG. 17 represents the effect of 30 and 60 nM LNA anti-miRNA 429-3p (LNA 429) or of 60 nM control anti-miRNA LNA (LNA CTA) transfected 72 h in BT474, a HER2+ breast cancer cell line, on HER2 activation (pYHER2) and expression (HER2), as well as on the activation of Akt (pAkt) and ERK (pERK) and on Clathrin level of expression analyzed by western blot.

Figure 18:
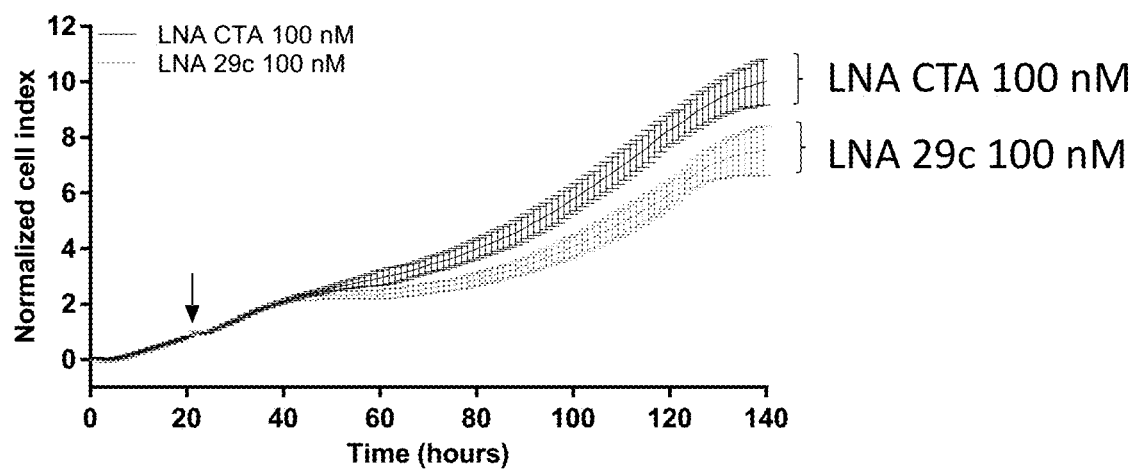

FIG. 18 represents the effect of 100 nM LNA anti-miRNA 29c-3p (LNA 29c) or of 100 nM control anti-miRNA LNA (LNA CTA) transfected in SKBR3, a HER2+ breast cancer cell line, on HER2-dependent proliferation measured in real-time by an impedance-based cellular growth assay (xCELLigence).

Figure 19:
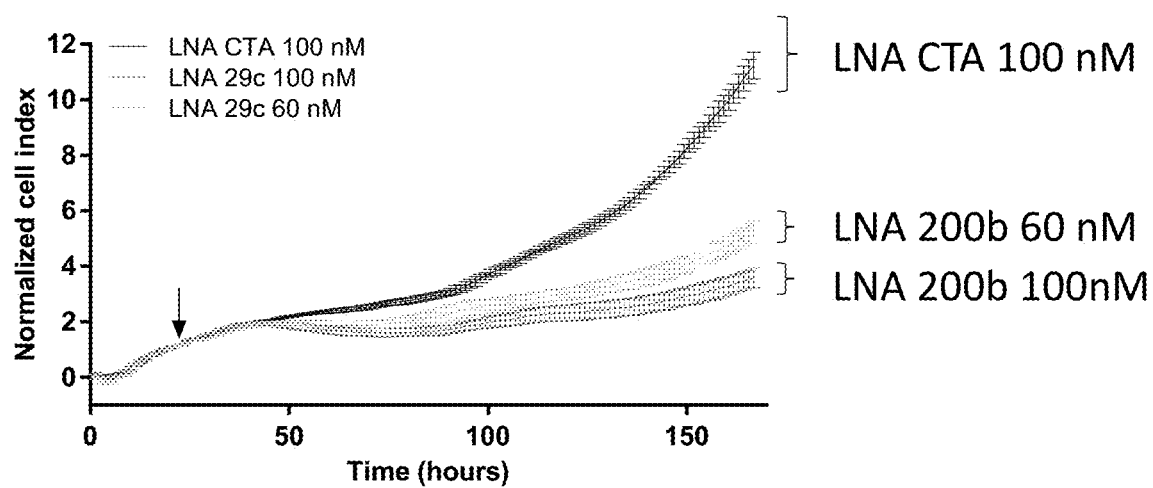

FIG. 19 represents the effect of 60 and 100 nM LNA anti-miRNA 29c-3p (LNA 29c) or of 100 nM control anti-miRNA LNA (LNA CTA) transfected in BT474, a HER2+ breast cancer cell line, on HER2-dependent proliferation measured in real-time by an impedance-based cellular growth assay (xCELLigence).

Figure 20:
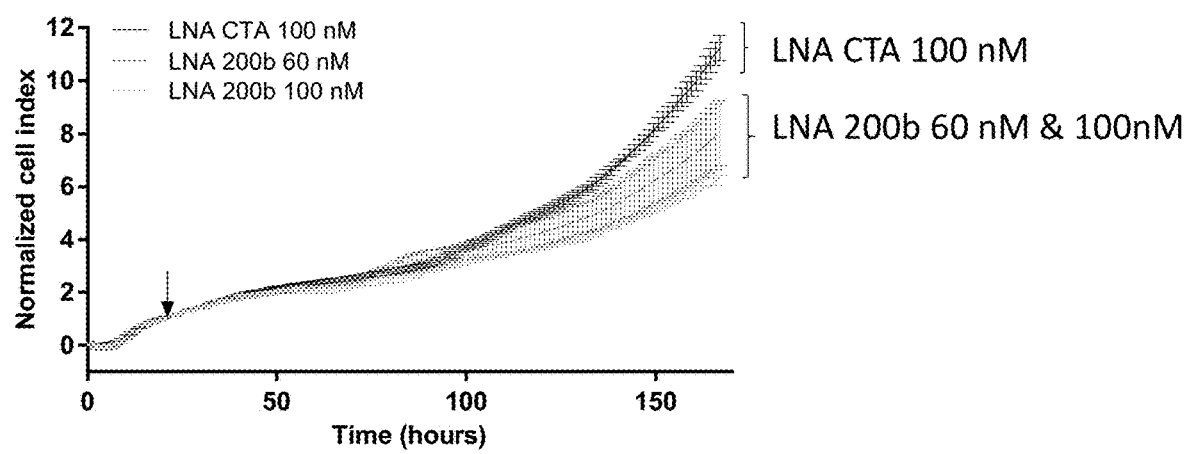

FIG. 20 represents the effect of 60 and 100 nM LNA anti-miRNA 200b-3p (LNA 200b) or of 100 nM control anti-miRNA LNA (LNA CTA) transfected in BT474, a HER2+ breast cancer cell line, on HER2-dependent proliferation measured in real-time by an impedance-based cellular growth assay (xCELLigence).

Figure 21:
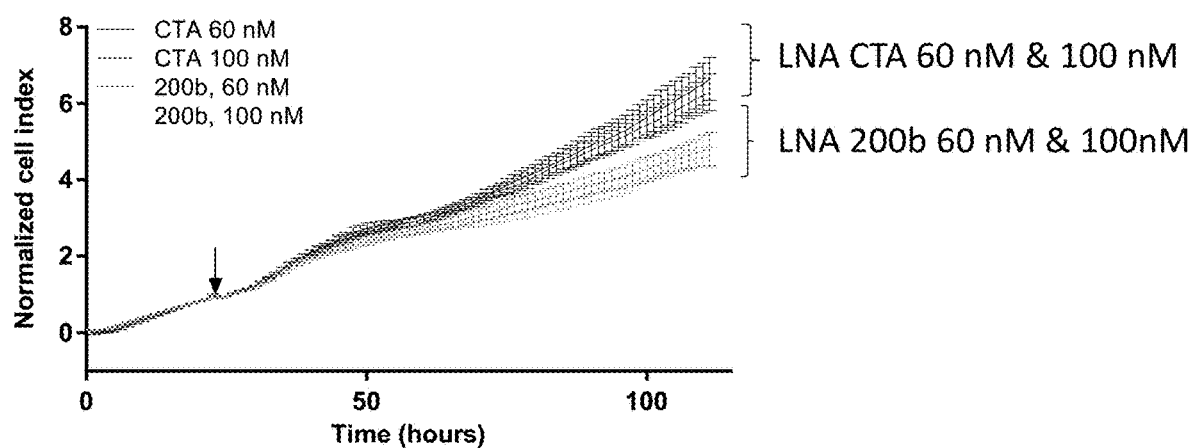

FIG. 21 represents the effect of 60 nM and 100 nM LNA anti-miRNA 200b-3p (LNA 200b) or control anti-miRNA LNA (LNA CTA) transfected in SKBR3, a HER2+ breast cancer cell line, on HER2-dependent proliferation measured in real-time by an impedance-based cellular growth assay (xCELLigence).

Figure 22:
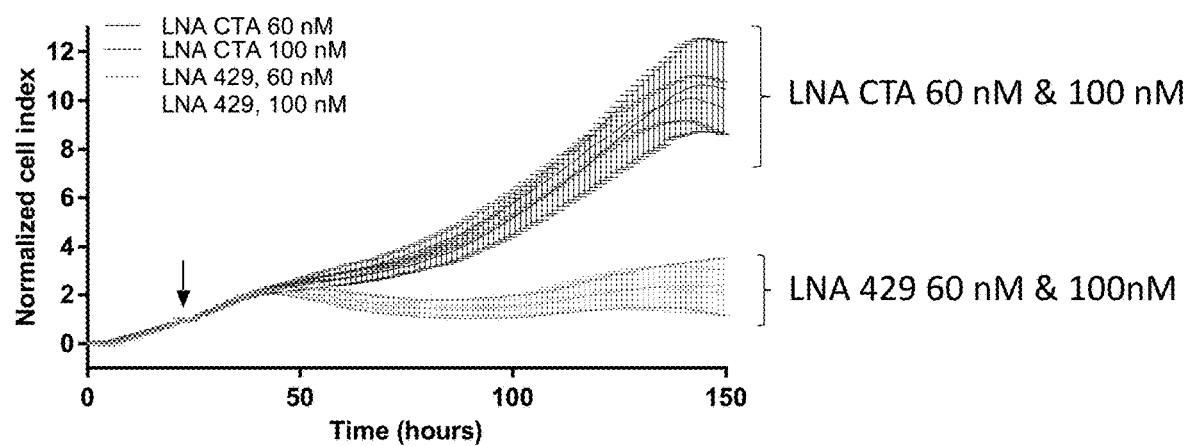

FIG. 22 represents the effect of 60 and 100 nM LNA anti-miRNA 429-3p (LNA 429) or control anti-miRNA LNA (LNA CTA) transfected in SKBR3, a HER2+ breast cancer cell line, on HER2-dependent proliferation measured in real-time by an impedance-based cellular growth assay (xCELLigence).

Figure 23:
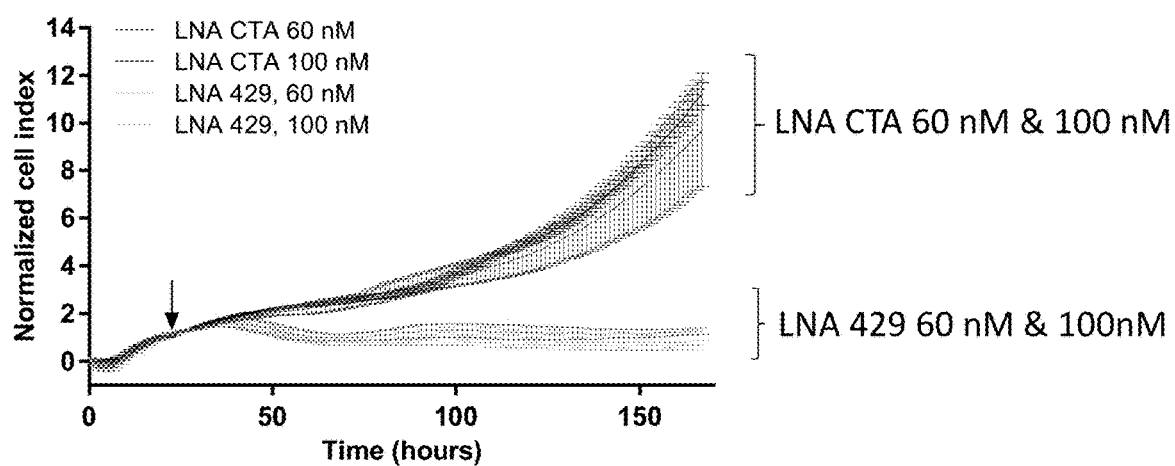

FIG. 23 represents the effect of 60 and 100 nM LNA anti-miRNA 429-3p (LNA 429) or control anti-miRNA LNA (LNA CTA) transfected in BT474, a HER2+ breast cancer cell line, on HER2-dependent proliferation measured in real-time by an impedance-based cellular growth assay (xCELLigence).

Figure 24:
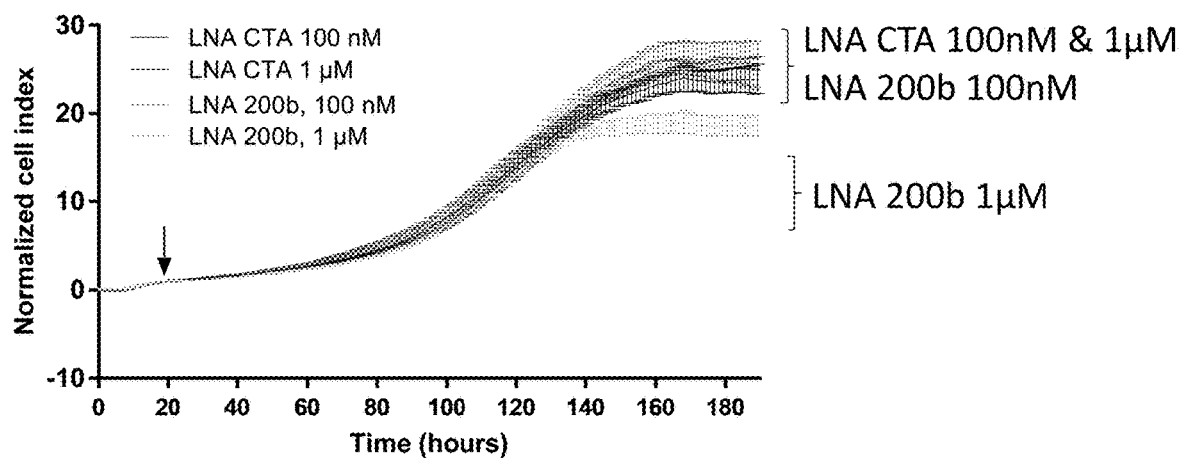

FIG. 24 represents the effect 0.1 and 1 µM LNA anti-miRNA 200b-3p (LNA 200b) or control anti-miRNA LNA (LNA CTA) delivered by gymnosis in BT474, a HER2+ breast cancer cell line, on HER2-dependent proliferation measured in real-time by an impedance-based cellular growth assay (xCELLigence).

Figure 25:
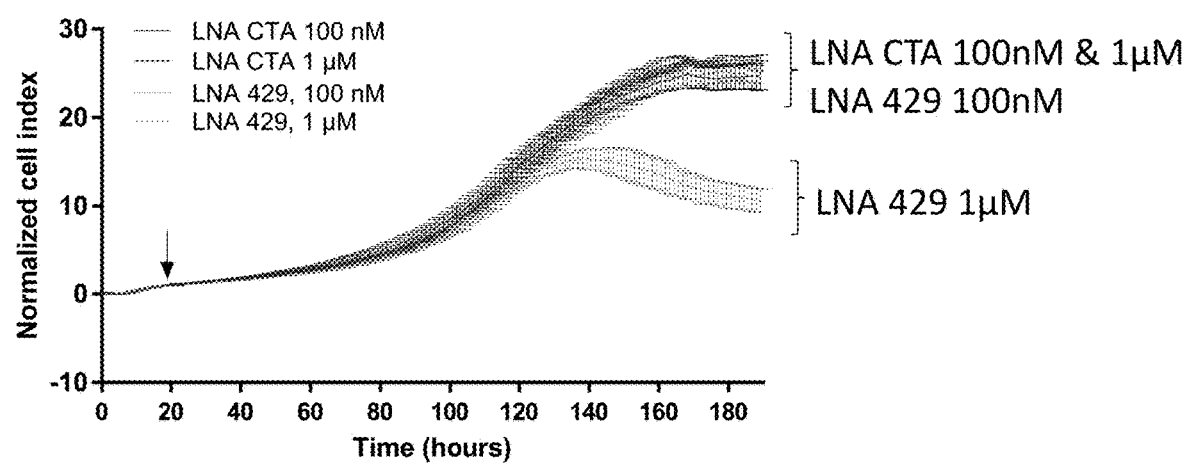

FIG. 25 represents the effect 0.1 and 1 µM LNA anti-miRNA 429-3p (LNA 429) or control anti-miRNA LNA (LNA CTA) delivered by gymnosis in BT474, a HER2+ breast cancer cell line, on HER2-dependent proliferation measured in real-time by an impedance-based cellular growth assay (xCELLigence).

Figure 26:
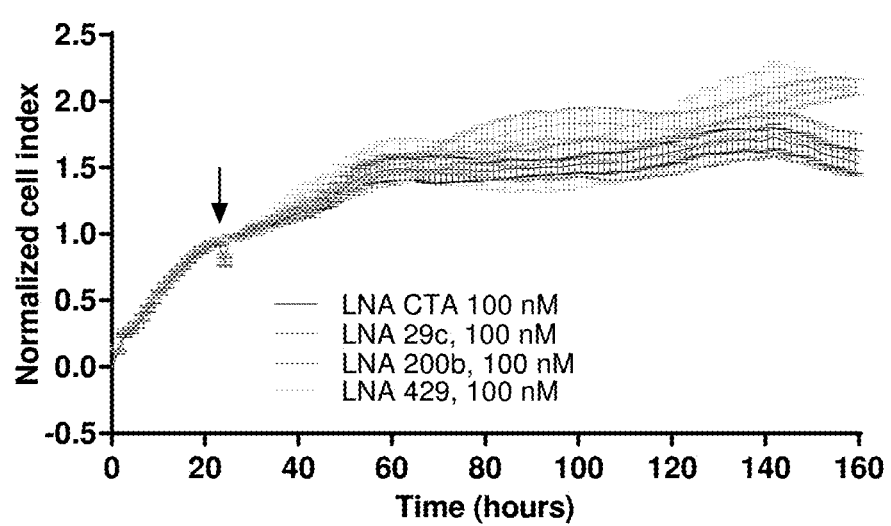

FIG. 26 represents the effect of 100 nM LNA anti-miRNA 29c-3p (LNA 29c), LNA anti-miRNA 200b (LNA 200b), LNA anti-miRNA 429-3p (LNA 429) or control anti-miRNA LNA (LNA CTA) transfected in MDAMB-231, a HER2-negative breast cancer cell line, on cell proliferation measured in real-time by an impedance-based cellular growth assay (xCELLigence).

Figure 27B:
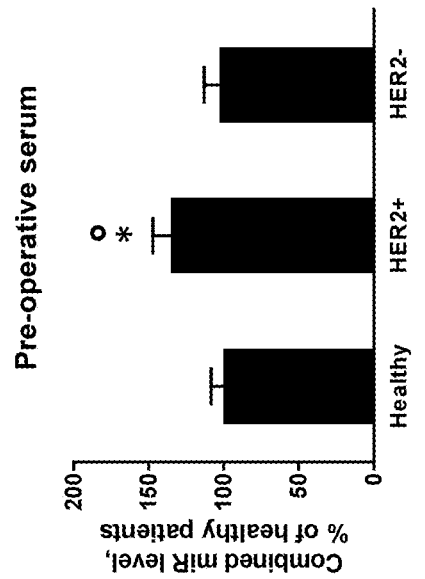
Figure 27A:
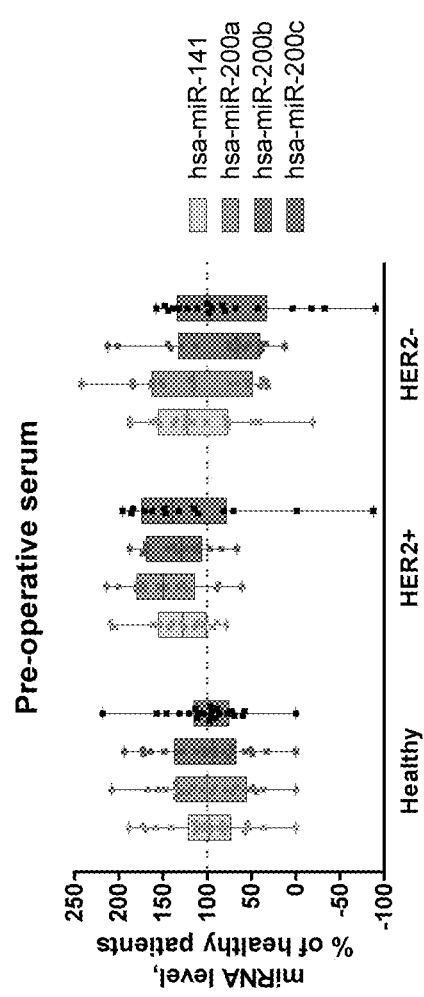

FIGS. 27A-27B represent the level of expression of miR-141-3p, miR-200a-3p, miR-200b-3p, miR-200c-3p in pre-operative serum samples derived from healthy individuals (n=22), HER2+ breast cancer patients (n=14) or HER2− breast cancer patients (n=18). Individual miRNA level of expression is shown in the left panel. Combined miRNA level of expression is shown in the right panel.

In the figures and examples "miR" and "miRNA" are used interchangeably, e.g. "miR 429-3p" means "miRNA 429-3p".

EXAMPLES

Example 1

Methods Used in the Examples

METHODS:
Datasets and Survival analysis

The effect of miRNAs on the overall survival of breast cancer patients was measured using miRpower [Breast] (kmplot.com/analysis/index.php?p=service&cancer=breast_miRna) on the METABRIC (1262 breast tumors). Analyses were either performed on HER2 positive status (HER2+ by Immunohisto chemistry (IHC) on molecular subtype HER2+ER) or performed on HER2− (Triple negative breast cancers (TNBC) molecular subtype) breast cancer patients.

Cell Lines and Culture Conditions

HER2+ breast cancer cell line SKBR3 (ATCC HTB-30) and BT474 (ATCC HTB-20) as well as HER2− breast cancer cell line MDAMB-231 (ATCC CRM-HTB-26) were cultured in DMEM (4.5 g/l glucose; Gibco) supplemented with 10% fetal bovine serum (FBS), 10 mM Hepes (Gibco) and 1% penicillin/streptomycin. The cells were cultured in 100 mm Petri-dishes containing 10 mL complete medium at 37° C. in a humidified incubator supplemented with 5% $CO_2$.

Reagents

Primary antibodies used were anti-pY1248 HER2 (#06-229, Millipore; 1:1000), anti-HER2 (ab2428, Abcam; 1:1000), anti-pAKT and anti-pERK1/2 (#9271; 1:100 and #9106L; 1:1000, respectively, Cell Signaling Technology), anti-clathrin (BD Biosciences #610500; 1:1000). Secondary antibodies were anti-rabbit (#NA9340-1ML GE Healthcare) or mouse IgG (#NA9310-1ML GE Healthcare) coupled with HRP (1:5000). The anti-MSN and anti-Ezrin were a gift from Dr. Paul Mangeat (Université de Montpellier) and were used at a 1:1000 dilution. MiRNAs mimics and anti-miRNA (antagomiR) were purchased from Active Motif® and were as followed: miRNA 29c-3p mimic (MIM0080), miRNA 29c-3p inhibitor (INH0080), miRNA 200b-3p inhibitor (INH0252) and miRNA 429-3p inhibitor (INH0388).

miRCURY LNA miRNA Inhibitor (LNA) were purchased from Exiqon/Qiagen® and were as followed: miRNA 29c-3p inhibitor (CCGATTTCAAATGGTGCT—SEQ ID NO: 30, YI04105460), miRNA 200b inhibitor (CATCAT-TACCAGGCAGTATT—SEQ ID NO: 31, YI04104042), miRNA 429-3p inhibitor (CGGTTTTACCAGACAGT-ATT—SEQ ID NO: 32, YI04101290) and control miRNA inhibitor (TAACACGTCTATACGCCCA—SEQ ID NO: 33, YI00199006).

miRNA Mimics and Anti-miRNA Transfection

MiRNA-200b-3p, miRNA-429-3p and miRNA-29c-3p (UAAUACUGCCUGGUAAUGAUGA—SEQ ID NO: 6, UAAUACUGUCUGGUAAAACCGU—SEQ ID NO: 1 and UAGCACCAUUUGAAAUCGGUUA—SEQ ID NO: 2 respectively) mimics or inhibitors (i.e. "anti-") were purchased from Active Motif or Exiqon/Qiagen. 250*10³ SKBR3 cells, BT474 cells or MDAMB-231 cells were cultured in antibiotic-free DMEM (10% FBS, 10 mM Hepes, Gibco) in 6 wells plates. or Exiqon/Qiagen. Twenty-four hours later, cells were transfected with 20-100 nM miRNA mimics or inhibitors by using Lipofectamine® RNAiMAX in Opti-MEM medium (Gibco) according to the manufacturer's instructions and processed for western blot or MTT assays 48 to 96 h after or impedance-based cell growth assay. The culture medium was replaced with DMEM 1% antibiotics 6 h after transfection.

RNA Extraction, cDNA Preparation and Quantitative Real Time RT-PCR Analysis

Total RNA was extracted from cells using Tri Reagent® (Sigma T9424). The concentration and integrity of total RNA were measured using a NanoDrop 2000 spectrophotometer (Thermo Scientific, Wilmington, Del.). Reverse transcription reactions were performed with 200 ng total RNA using SuperScript™ II RT after RNaseOUT™ treatment (Thermo Scientific, Wilmington, Del.). Real time quantitative PCR (qRT-PCR) was performed in 10 µl using SYBR Green I Master kit (Roche Life Science) according to the manufacturer's instructions on a LightCycler 480 Instrument II.

The PCR primers were:

```
Forward MSN
                                              (SEQ ID NO: 24)
5'-GGAATGAGACAGGACCTAGGATATCTT-3'

Reverse MSN
                                              (SEQ ID NO: 25)
5'-GGAATGAGACAGGACCTAGGATATCTT-3'

Forward HER2
                                              (SEQ ID NO: 26)
5'-GCCGCAGTGAGCACCAT-3

Reverse HER2
                                              (SEQ ID NO: 27)
5'-CGCAGCTTCATGTCTGTGC-3'

Forward GAPDH
                                              (SEQ ID NO: 28)
5'-GATCCCTCCAAAATCAAGTGG-3'

Reverse GAPDH
                                              (SEQ ID NO: 29)
5'-GCAAATGAGCCCCAGCCTTCTC-3'
```

The PCR conditions were: 95° C., 10 s; 60° C., 10 s; 72° C., 15 s. At the conclusion of each run, a melt curve analysis was performed to ensure that a single product had been synthesized. The relative expression of HER2 and MSN, normalized to GAPDH, was calculated using the $2^{-\Delta\Delta Ct}$ method. The HER2 and MSN mRNA level analysis was performed on 25 breast cancer cell lines with various HER2 status: MDA-MB-361 (ATCC HTB-27), BT-483 (ATCC HTB-121), MDA-MB-453 (ATCC HTB-131), MDA-MB-415 (ATCC HTB-128), ZR-75-1 (ATCC CRL-1500), HCC202 (ATCC CRL-2316), BT-474 (ATCC HTB-20), MCF 10A (ATCC CRL-10317), MCF-12A (ATCC CRL-10782), MDA-MB-436 ATCC HTB-130, hTERT-HME1 (ATCC, CRL-4010), MCF-10-2A (ATCC CRL-10781), 18465 (ATCC CRL-8799), BT-549 (ATCC HTB-122), HCC1937 (ATCC CRL-2336), Hs 578T (ATCC HTB-126), MDA-MB-231 (ATCC HTB-26), MCF-12F (ATCC CRL-10783), PMC42 (RRID:CVCL_5215), MDA-MB-157 (ATCC HTB-24), BT-20 (ATCC HTB-19), HCC70 (ATCC CRL-2315), HCC1599 (ATCC CRL-2331), HCC1143 (ATCC CRL-2321) and HCC1187 (ATCC CRL-2322).

Western Blot

SKBR3, BT474 and MDAMB-231 cells were lysed (50 mM Tris, 25 mM NaCl, 1 mM EDTA, 1% Triton, 10% glycerol, pH 8.8 with leupeptin, aprotinin and pepstatin protease inhibitors and orthovanadate and AEBSF phosphatase inhibitors 10 min at 4° C. Lysates were denatured with Laemmli buffer 10 min at 95° C. and proteins were separated on 10% SDS/polyacrylamide gels (ProSieve, Lonza) in gradient buffer (100 mM Tris, 100 mM Tricine, 0.1% SDS), and transferred onto nitrocellulose membranes (Whatman®) using transfert buffer (20% EtOH, 25 mM Tris, 192 mM Glycine pH 8,5) according to standard protocols. Membranes were blocked using 3% BSA in TBST buffer (140 mM NaCl, 3 mM KCl, 25 mM Tris, 0.1% Tween) 30 min at room temperature, and incubated over night at 4° C. with suitable primary antibodies (see Reagents). Horseradish peroxidase-conjugated anti-rabbit or anti-mouse antibody (see Reagents) was used as a secondary antibody. Detection was performed using the SuperSignal West Pico Chemiluminescent Substrate (Pierce) on the FUSION-FX7—SPECTRA acquisition system (Vilber Lourmat).

miRnome Analysis

MiRNA expression levels were quantified by RT-PCR using the SYBR Green Master Mix kit on the ABI Prism 7900 Sequence Detection System (Perkin-Elmer Applied Biosystems, Foster City, Calif.). The Human miScript Primer Assays version 9.0 and 11.0 from Qiagen, designed to detect 804 human miRNA probes, were used according to the manufacturer's guidelines. Small nucleolar RNA RNU44 (Qiagen) was used as endogenous control to normalize miRNA expression levels.

MTT Assay

5*10³ SKBR3 cells or BT474 cells were cultured in 96 wells plates. At 72 h, the medium was removed and replaced with 100 μL of fresh culture medium. 10 μL of the 12 mM MTT stock solution were added to each well and to 100 μL of medium alone as a negative control. After 2-4 h incubation at 37° C., all but 25 μL of medium from the wells was removed and 50 μL of DMSO was added. Absorbance at 540 nm is read and cell proliferation is quantified.

Impedance-Based Cell Growth Assay 7-9.10³ cells/well were seeded into 200 μL of media in 96X microplates (E-Plate). The attachment, spreading and proliferation of the cells were monitored every 15 minutes using the RTCA-MP xCELLigence® system. Cell-sensor impedance was expressed as an arbitrary unit called the Cell Index.

Anti-miRNA (LNA Inhibitors)

| Targeted MiRNA | Nucleotide sequence | Commercial reference (Qiagen) | SEQ ID NO |
|---|---|---|---|
| miRNA 29c-3p | CCGATTTCAAATGGTGCT | YI04105460 | 30 |
| miRNA 200b-3p | CATCATTACCAGGCAGTATT | YI04104042 | 31 |
| miRNA 429-3p | CGGTTTTACCAGACAGTA | YI04101290 | 32 |
| Control anti miR LNA inhibitor | TAACACGTCTATACGCCCA | YI00199006 | 33 |

Datasets and miRNA Expression Level Analysis in Serum Sample from Healthy Subjects or Breast Cancer Patient The level of expression of miR-141-3p, miR-200a-3p, miR-200b-3p, miR-200c-3p in pre-operative serum samples derived from healthy individuals (n=22), HER2+ breast cancer patients (n=14) or HER2− breast cancer patients (n=18) was obtained from the study GSE42128 (Gene Expression Omnibus accession number) on array express database (www.ebi.ac.uk/arrayexpress/). miRNA expression was normalized to the mean value of corresponding Healthy controls. The mean value of their combined expression was also determined.

Example 2 miRnome Analysis of Breast Cancer Cell Lines with Different HER2 Status and Moesin Status Materials and Methods MiRNA expression levels in samples were quantified by quantitative RT-PCR (RT-qPCR) using the SYBR Green Master Mix kit on the ABI Prism 7900 Sequence Detection System as detailed in Example 1. Briefly, the Human miScript Primer Assays version 9.0 and 11.0 from Qiagen, designed to detect 804 human miRNA probes, were used according to the manufacturer's guidelines. The relative expression level of each miRNA, expressed as N-fold difference in target miRNA expression relative to RNU44. This analysis was performed in 25 breast cancer cell lines with different HER2 status (7 HER2+ and 18 HER2−) to monitor the level of several miRNAs, in particular miRNA 29, miRNA 200, miRNA 15 families as well as of miRNA-451a, miRNA-542-5p and miRNA 615-3p.

Results

Figure 1:
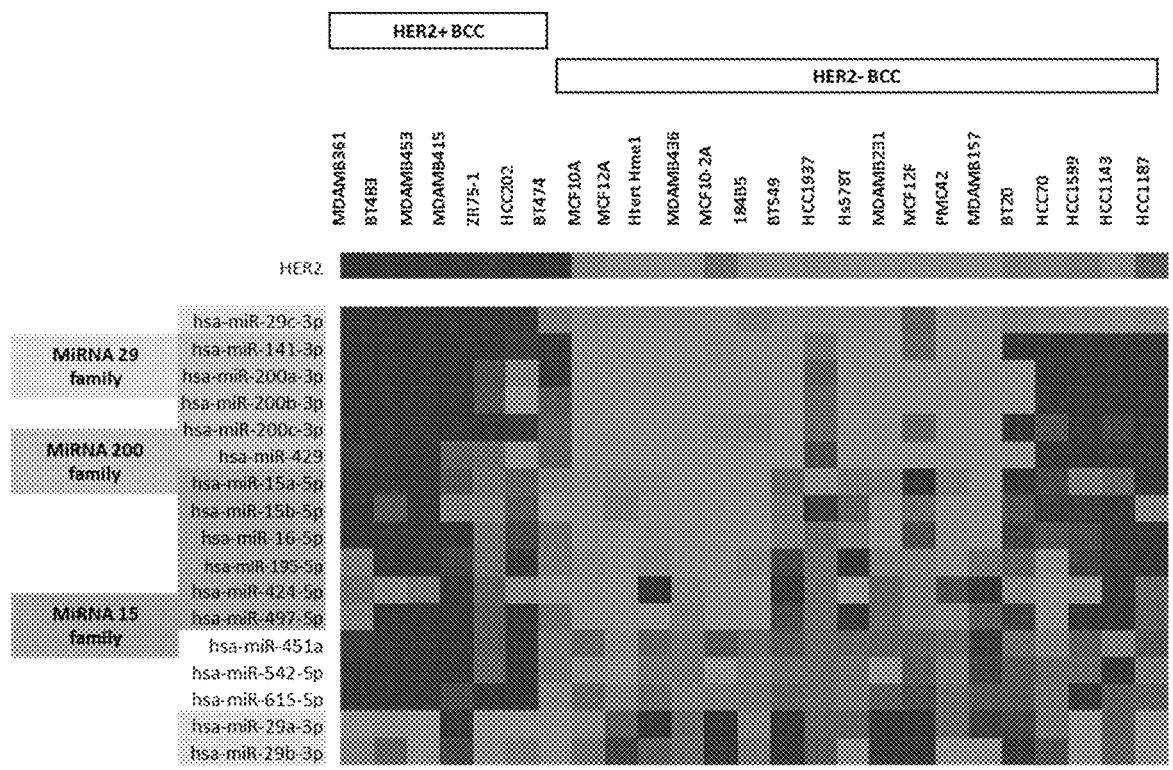
FIG. 1 represents miRnome analysis of some breast cancer cell lines with different HER2/MSN status. Transcriptome analysis showing the level of HER2 and Moesin (MSN) mRNA expression in breast cancer cell lines with different HER2/MSN status (CDS HER2+ MSN$^{lo}$ and CDS HER2− MSN$^{hi}$) is shown in the top panel. Representation of candidates miRNA expression is shown in the bottom panel.
Figure 2A:
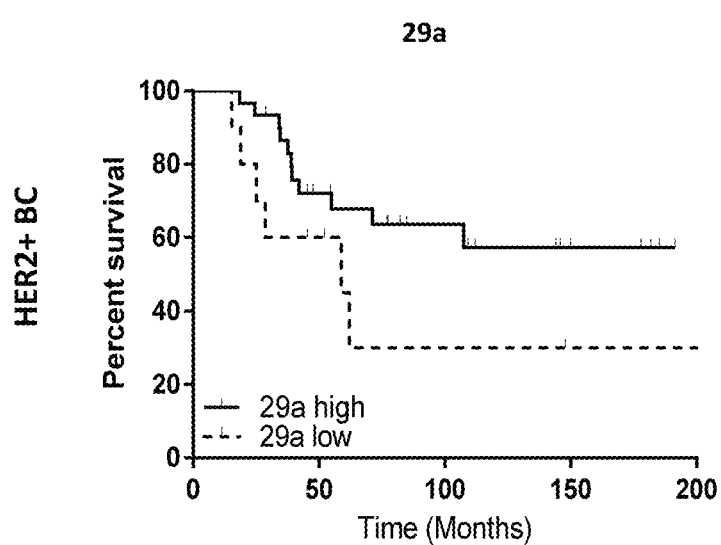
Figure 2B:
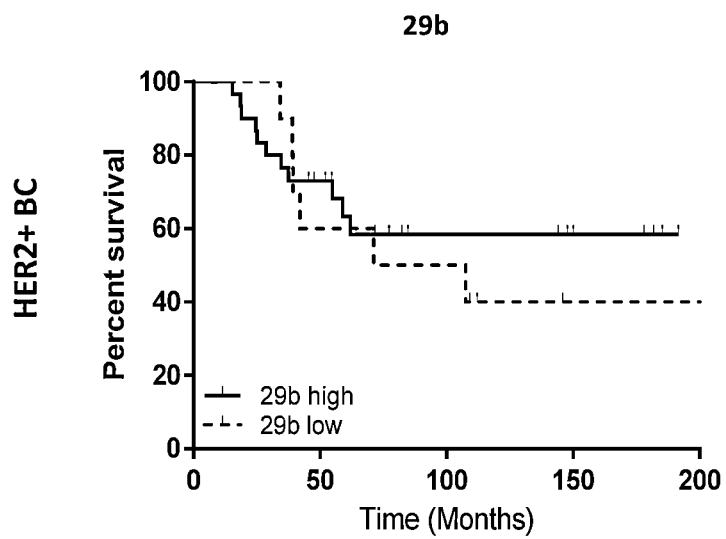
Figure 2C:
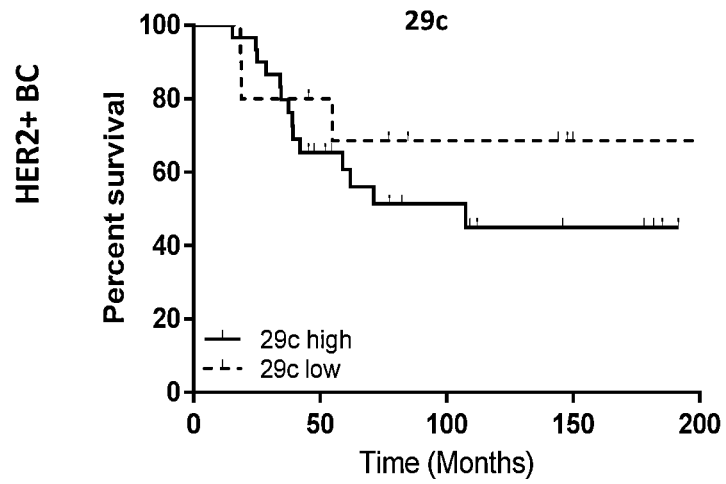
Figure 2D:
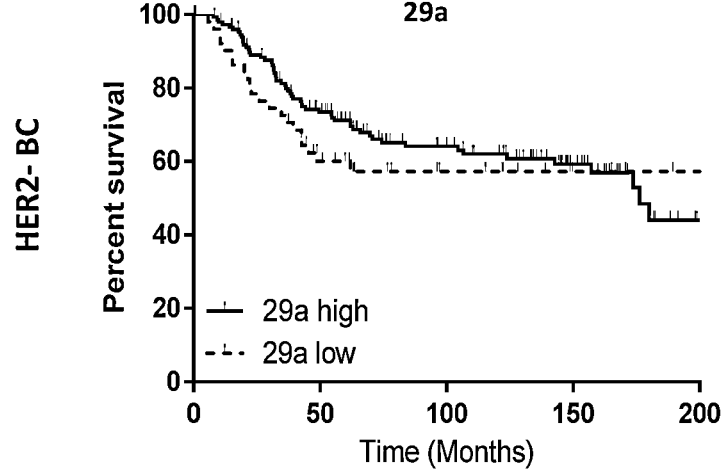
Figure 2E:
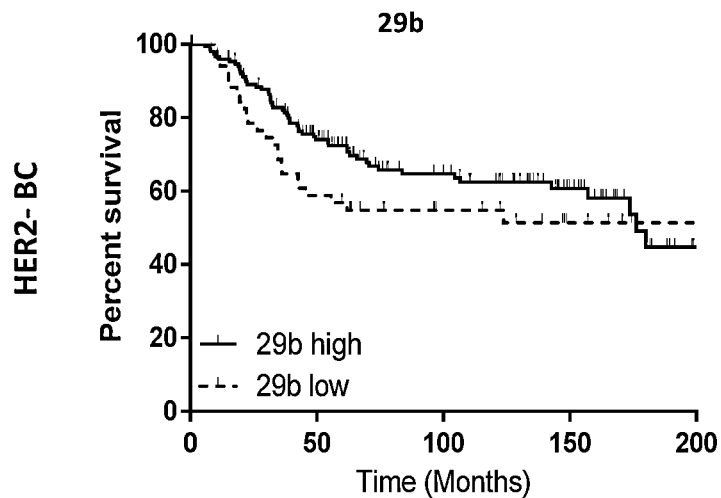
Figure 2F:
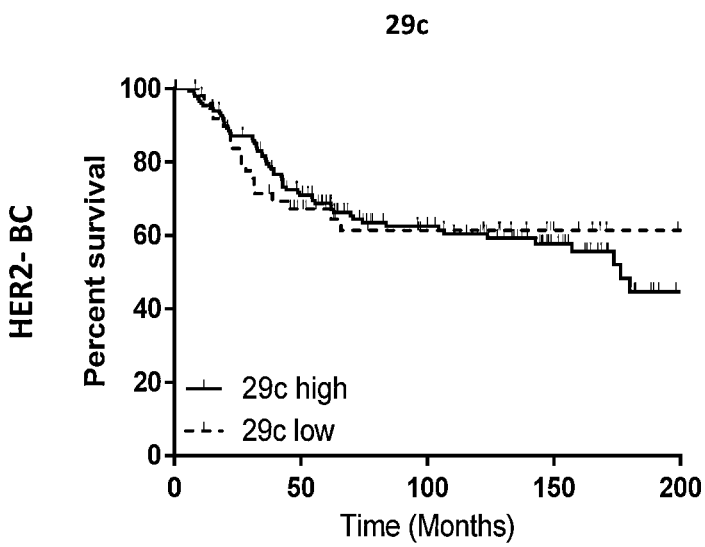
Figure 3A:
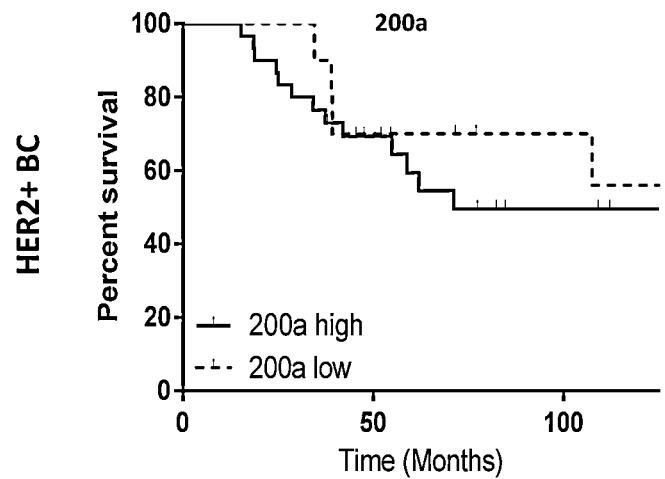
Figure 3B:
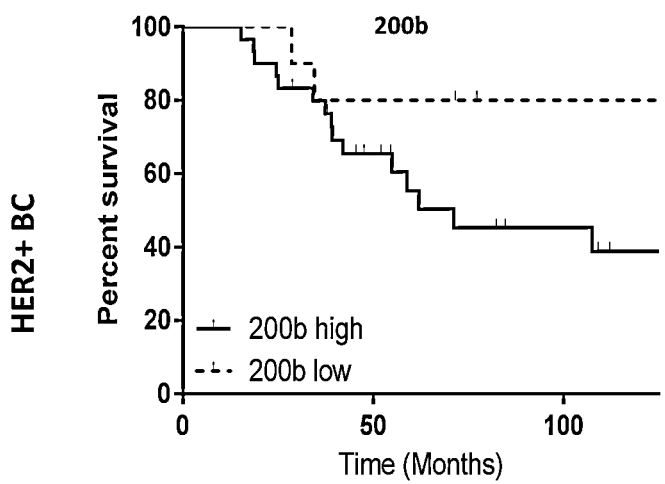
Figure 3C:
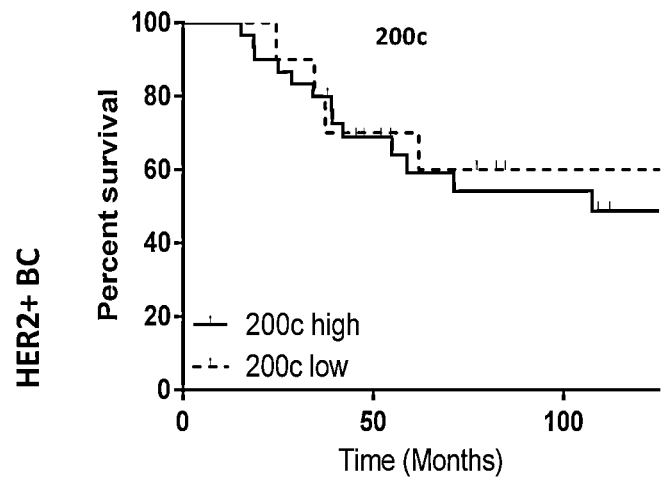
Figure 3D:
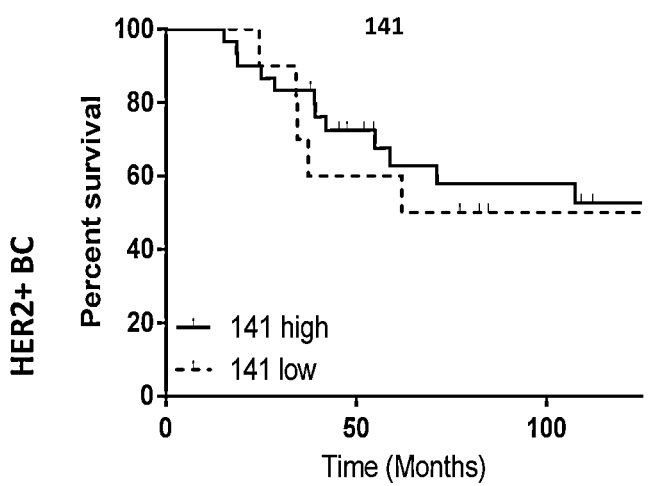
Figure 3E:
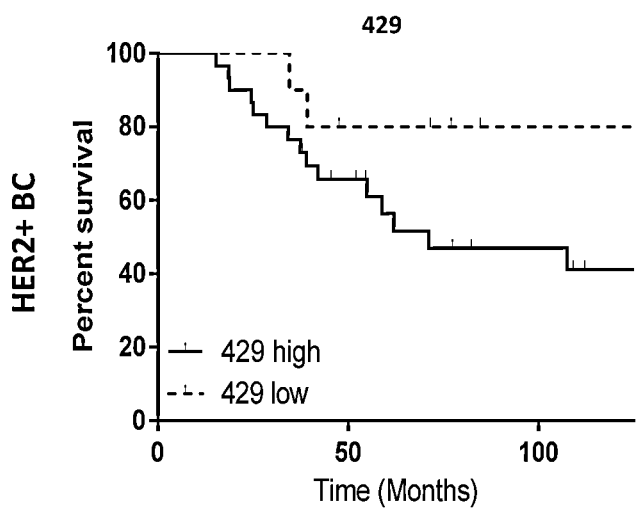
Figure 3F:
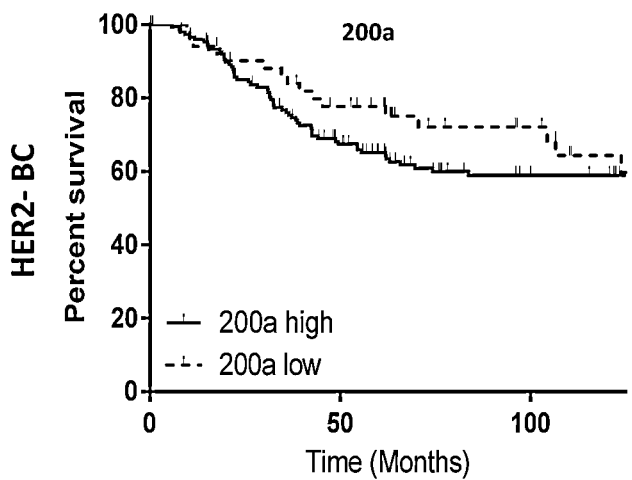
Figure 3G:
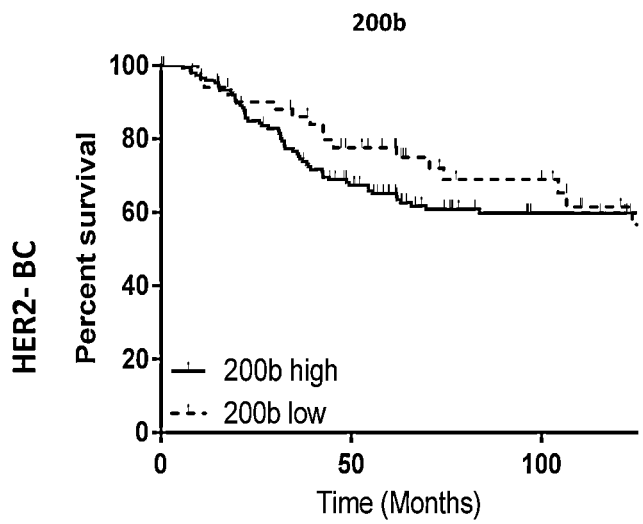
Figure 3H:
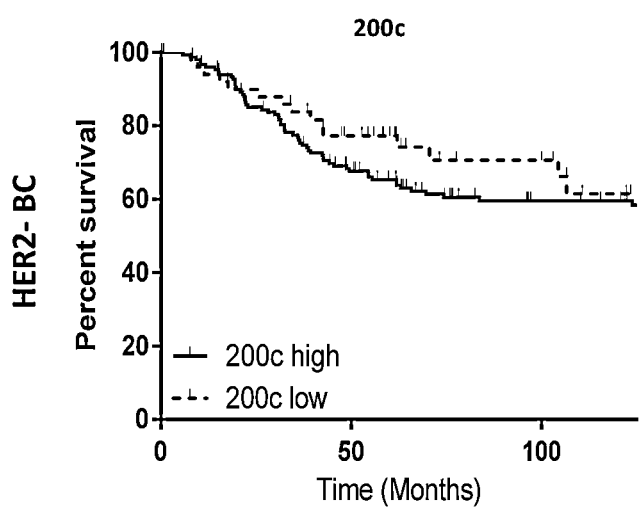
Figure 3I:
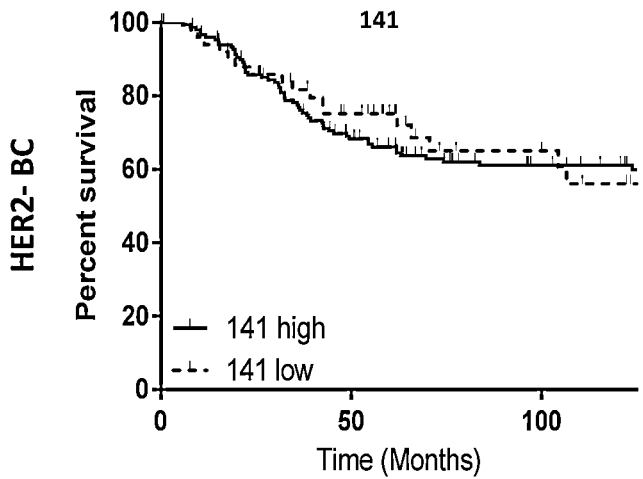
Figure 3J:
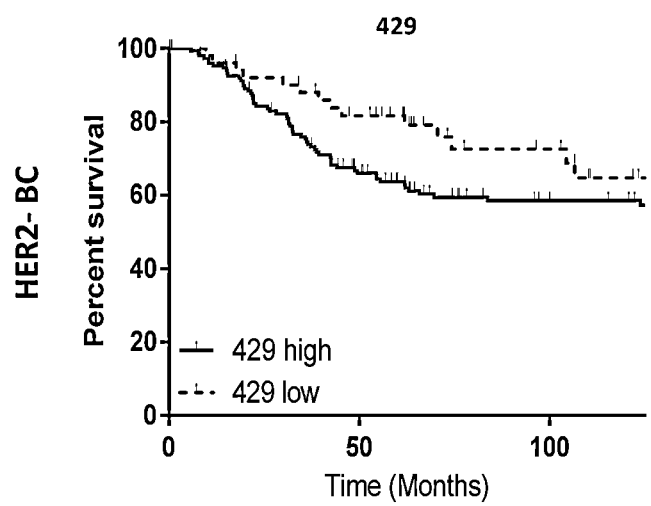
Figure 4A:
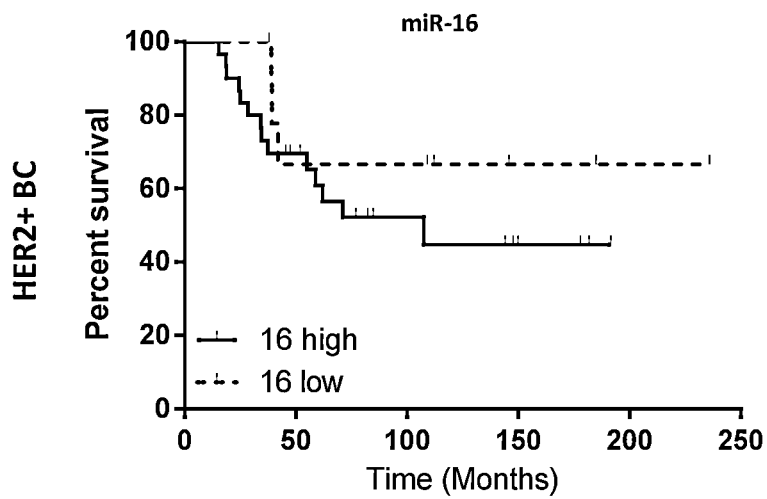
Figure 4B:
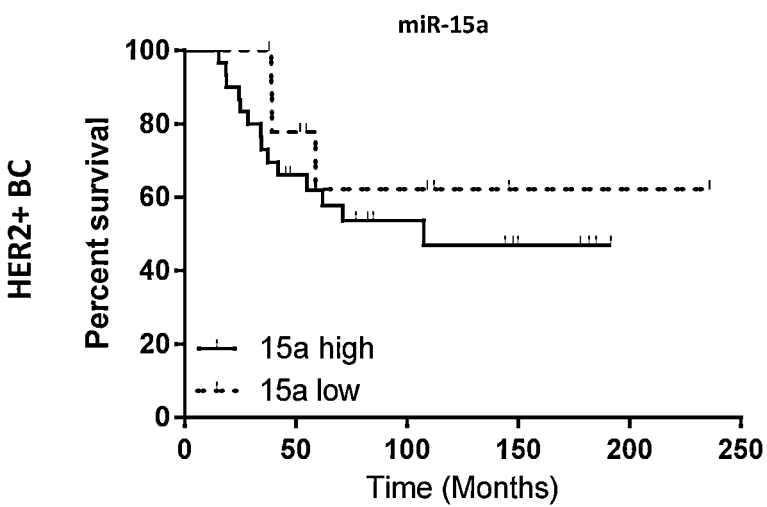
Figure 4C:
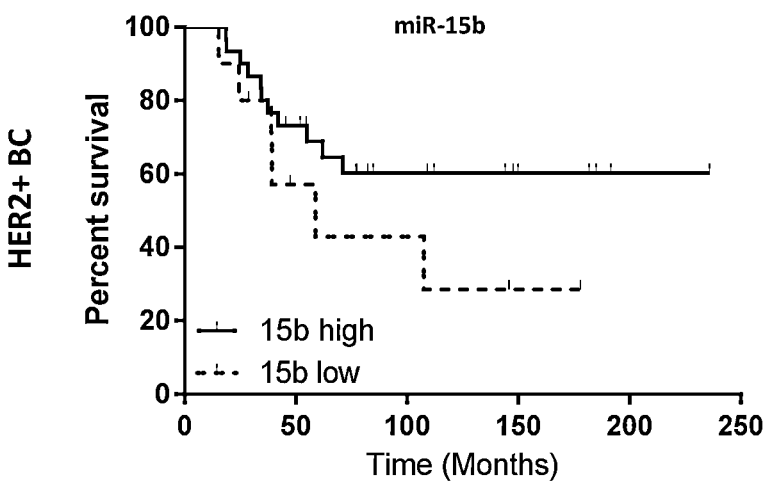
Figure 4D:
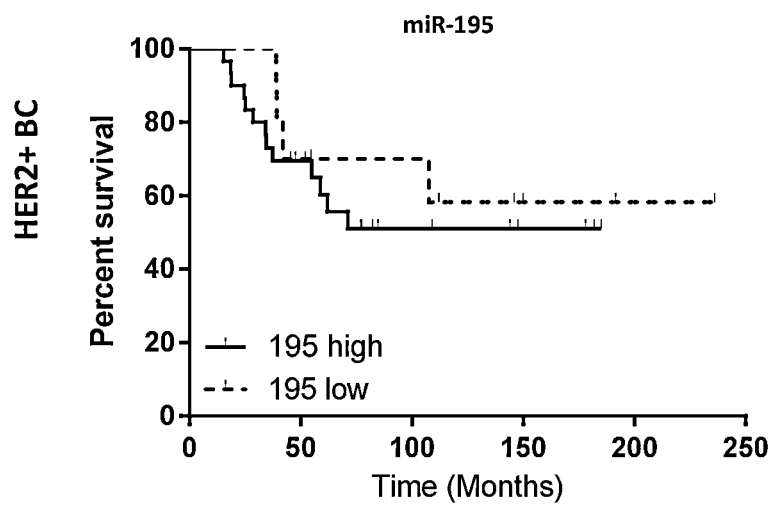
Figure 4E:
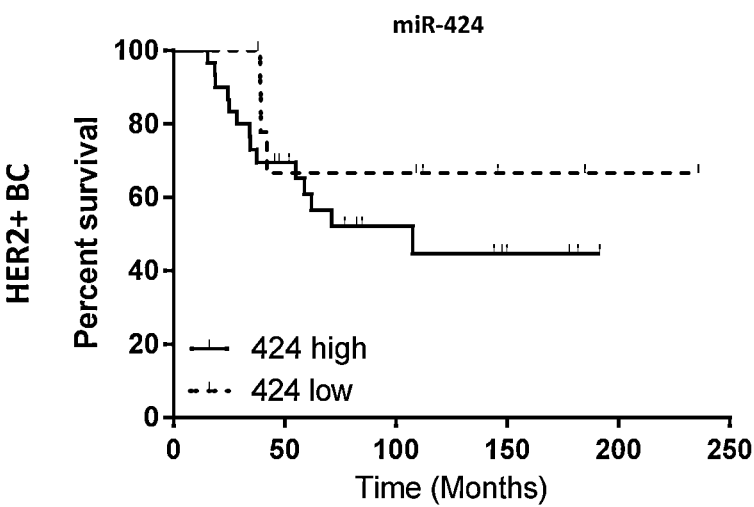
Figure 4F:
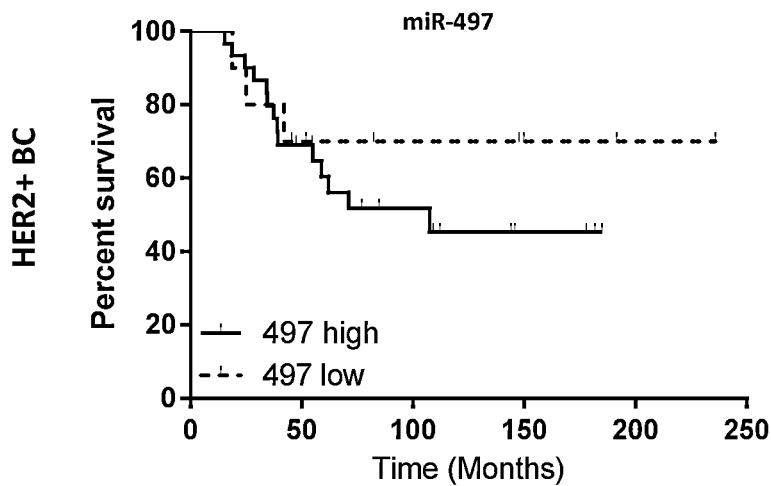
Figure 4G:
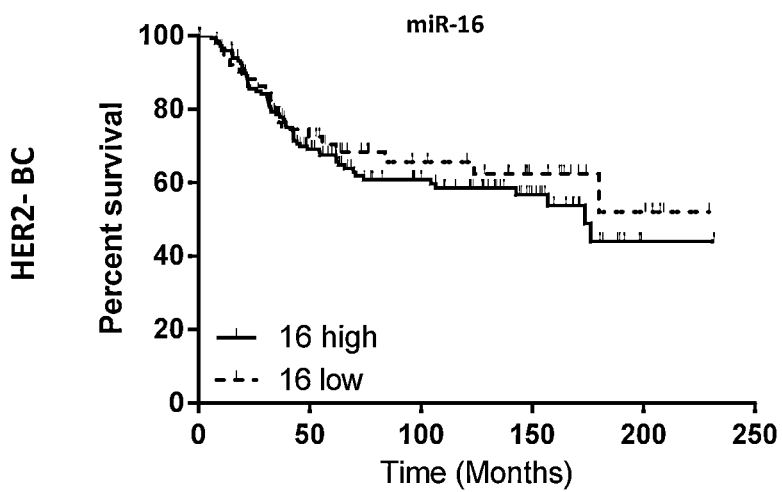
Figure 4H:
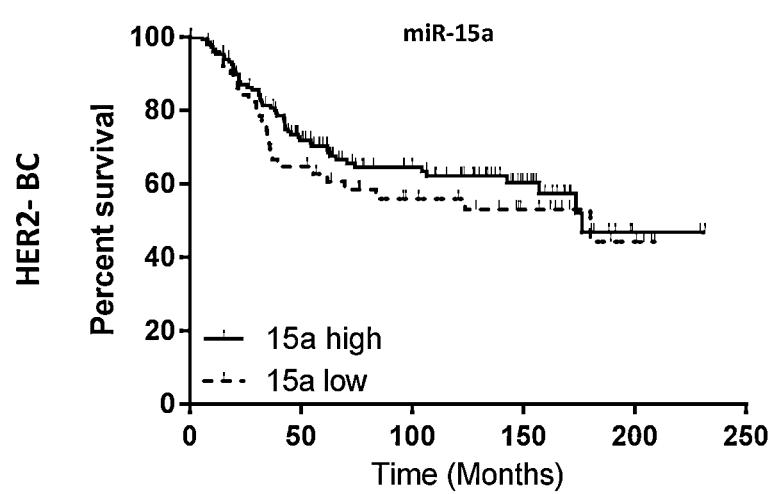
Figure 4I:
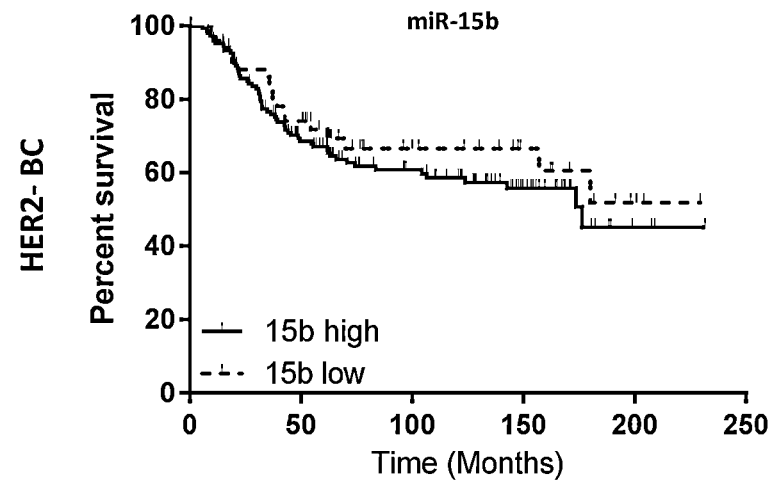
Figure 4J:
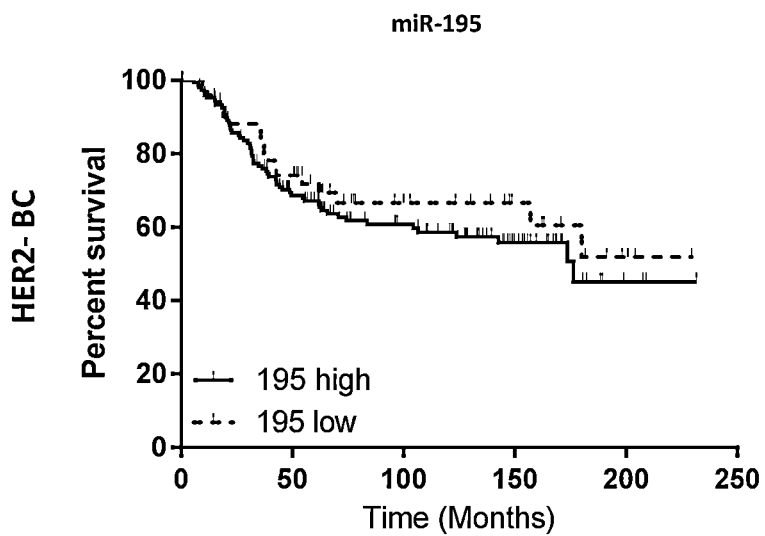
Figure 4K:
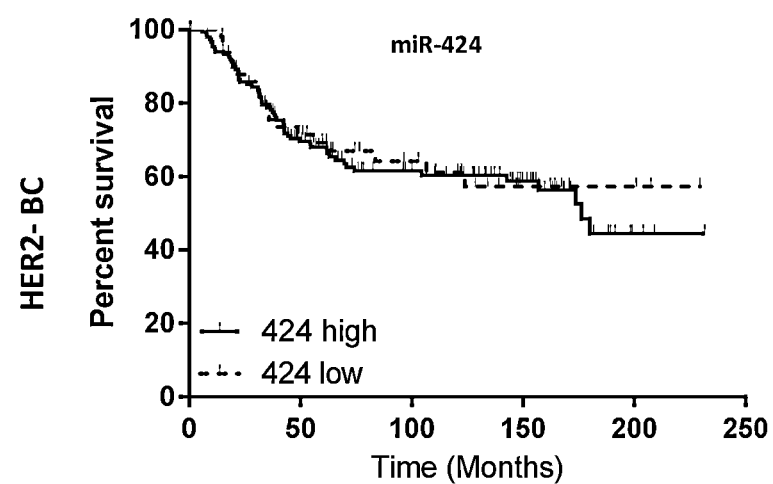
Figure 4L:
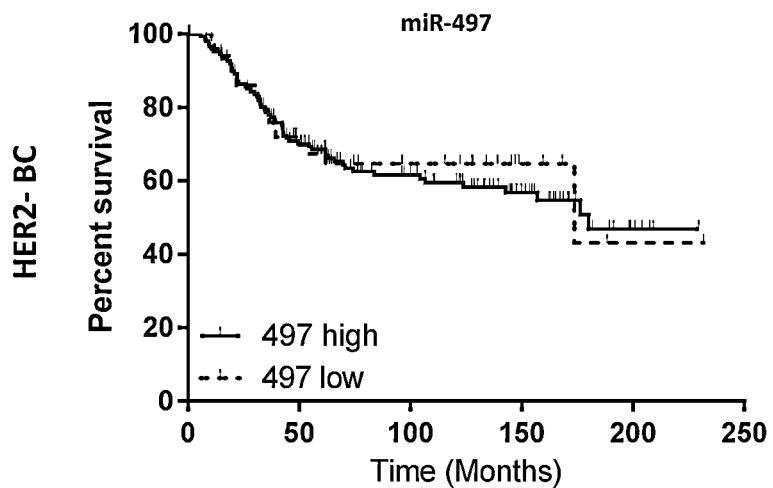
Figure 5A:
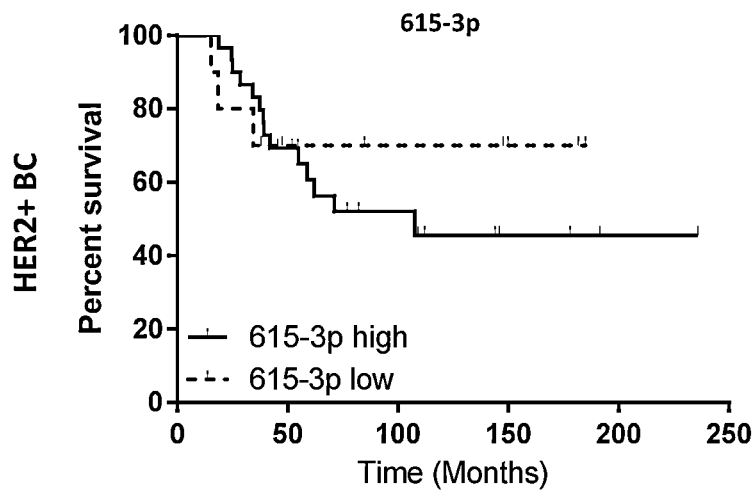
Figure 5B:
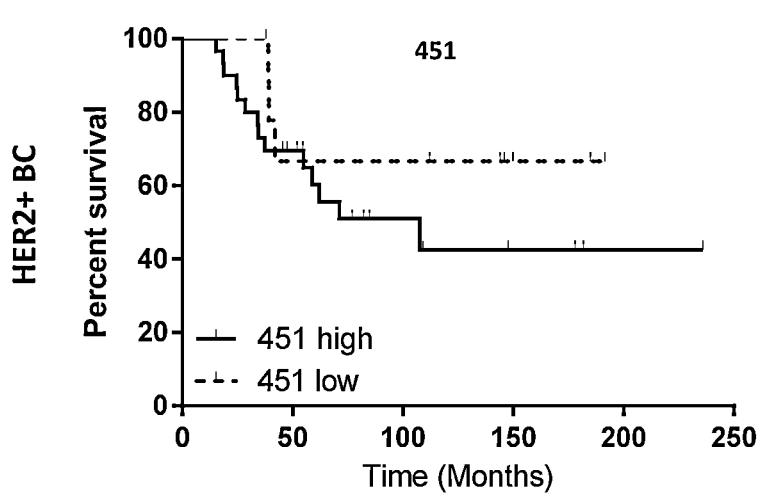
Figure 5C:
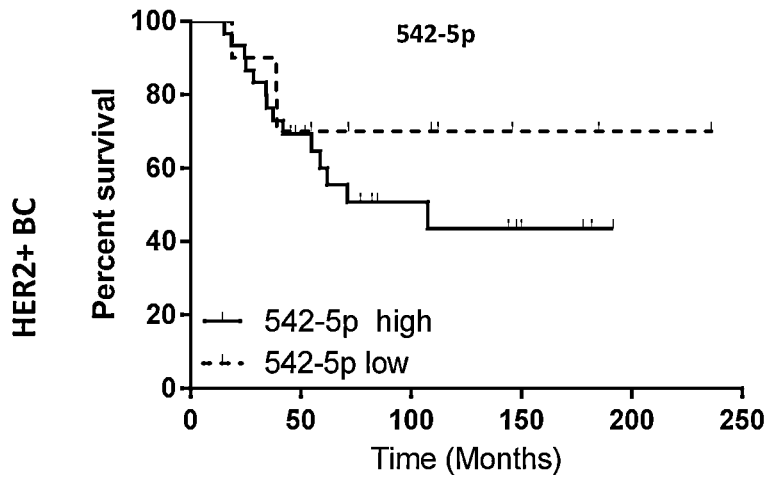
Figure 5D:
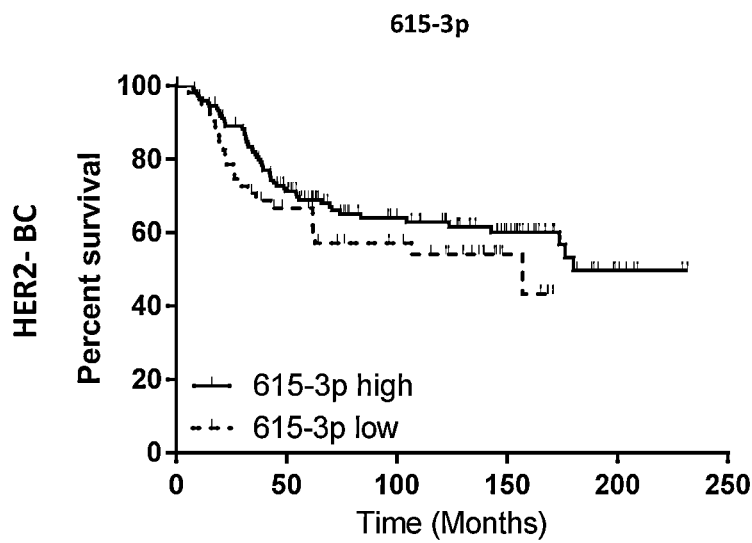
Figure 5E:
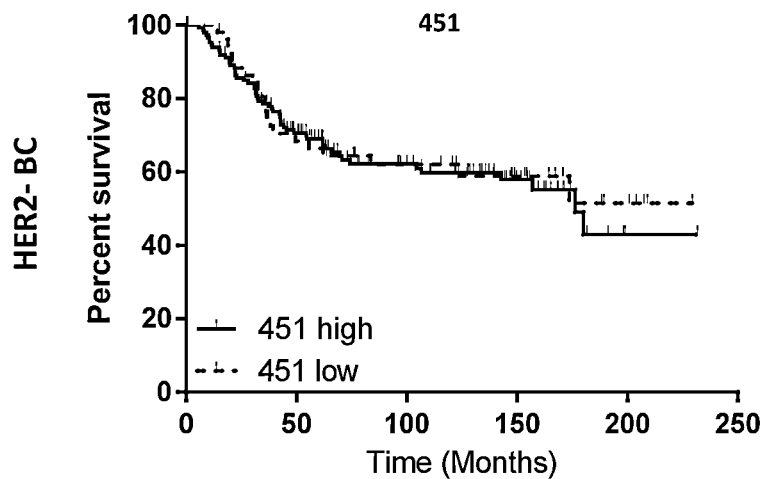
Figure 5F:
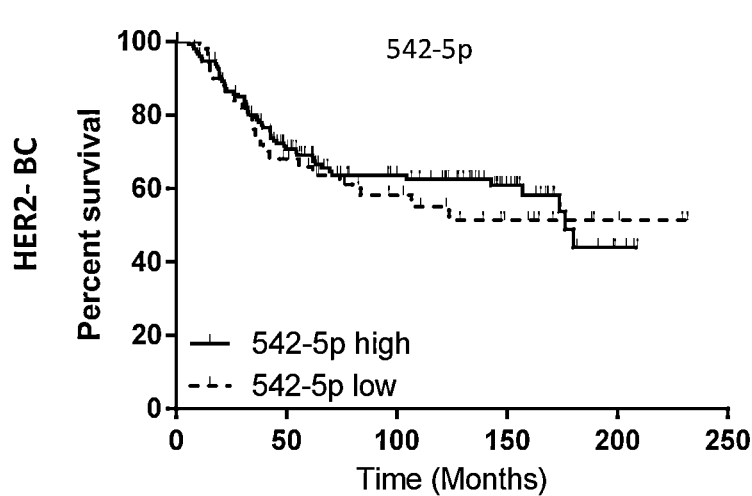

MiRnome analysis of the of the 25 breast cancer cell lines identified several miRNAs that were differentially expressed in HER2+ breast cancer cell lines compared to HER2− breast cancer cell lines, among which the miRNA 29 family (miRNA 29a-3p, miRNA 29b-3p and miRNA 29c-3p), the 5 members of miR200 family (miRNA 200a-3p, miRNA 200b-3p, miRNA 200c-3p, miRNA 141-3p and miRNA 429-3p), the 6 members of miR15 family (miRNA 15a-5p, miRNA 15b-5p, miRNA 16-5p, miRNA 195-5p, miRNA 424-5p and miRNA 497-5p) as well as miRNA 451a-5p, miRNA 542-5p and miRNA 615-3p (FIG. 1). The results are detailed in Table 3.

TABLE 3

| Family | miRNA | Fold increase | P value | |
|---|---|---|---|---|
| 29 | hsa-miR-29c-3p | 7.2 | <0.0001 | *** |
| | hsa-miR-29a-3p | 0.5 | 0.0124 | * |
| | hsa-miR-29b-3p | 0.7 | 0.1566 | ns |
| 200 | hsa-miR-141-3p | 4.5 | <0.0001 | *** |
| | hsa-miR-200a-3p | 3.1 | 0.0082 | ** |
| | hsa-miR-200b-3p | 2.8 | 0.0184 | * |
| | hsa-miR-200c-3p | 3.5 | 0.0002 | ** |
| | hsa-miR-429-3p | 2.3 | 0.0539 | ns |
| 15 | hsa-miR-15a-5p | 2.3 | 0.037 | * |
| | hsa-miR-15b-5p | 1.3 | 0.3324 | ns |
| | hsa-miR-16-5p | 2.3 | 0.0018 | ** |
| | hsa-miR-195-5p | 2.4 | 0.0231 | * |
| | hsa-miR-424-5p | 0.9 | 0.8105 | ns |
| | hsa-miR-497-5p | 2.6 | 0.0033 | ** |
| | hsa-miR-451a-5p | 1.5 | 0.0007 | ** |
| | hsa-miR-542-5p | 2.4 | <0.0001 | *** |
| | hsa-miR-615-3p | 1.8 | 0.001 | * |

Conclusion

The amount of key miRNAs (miRNA 29c-3p, miRNA 141-3p, miRNA 200a-3p, miRNA 200b-3p, miRNA 200c-3p, miRNA 429-3p, miRNA 15a-5p, miRNA 16-5p, miRNA 195-5p, miRNA 497, miRNA 615-3p, miRNA 451a-5p and miRNA 542-5p) was specifically increased in HER2+ breast cancer cell lines compared to HER2− breast cancer cell lines.

The amount of key miRNAs (miRNA 29a-3p, miRNA 29b-3p) was specifically decreased in HER2+ breast cancer cell lines compared to HER2− breast cancer cell lines Example 3

Survival Analyses of Patients with Breast Cancer Depending on miRNA 29 Family Level of Expression.

Materials and Methods

The effect of miRNA 29 family level of expression on the overall survival of breast cancer patients was measured using the online miRpower Kaplan-Meier plotter (kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ER) or performed on HER2− (Triple negative breast cancers (TNBC) molecular subtype) breast cancer patients.

Results

Low expression levels of miRNA 29a-3p and miRNA 29b-3p (downregulated in HER2+/MSN$^{lo}$ breast cancer cell lines, see Example 2) were associated with a trend towards shorter overall survival compared to patients having high expression levels of these miRNAs (FIG. 2 A-B).

MiR29a-3p:
Median survival: 61 months with low expression level of miRNA 29a-3p vs. more than 200 months with high expression level of miRNA 29a-3p,
Overall survival: more than 70% death with low expression level of miRNA 29a-3p compared to less than 40% death with high expression level of miRNA 29a-3p (P=0.11).

MiR29b-3p:
Median survival: 73 months with low expression levels of miRNA 29b-3p vs. more than 200 months with high expression level of miRNA 29b-3p
Overall survival: more than 60% death with low expression level of miRNA 29b-3p compared to less than 40% death with high expression level of miRNA 29b-3p (P=0.59).

A similar trend was observed for HER2− breast cancer patients (P=0.38 and 0.17) (FIG. 2 D-E).

On the contrary, high expression level of miRNA 29c-3p (upregulated in HER2+ breast cancer cell lines, see Example 1) were associated with a trend towards shorter overall survival compared to patients having low expression level of this miRNA (FIG. 2 C):
Median survival: 71 months with high expression level of miRNA 29c-3p vs. more than 200 months with low expression levels of miRNA 29c-3p
Overall survival: more than 55% death with high expression level of miRNA 29c-3p compared to less than 40% death with low expression level of miRNA 29c-3p (P=0.37)).

This trend was specific of HER2+ breast cancers, since level of expression of these miRNAs did not alter survival profiles of HER2− breast cancer patients (P=0.96) (FIG. 2 F).

Conclusion

Survival analyses demonstrated that, the contrary to miRNA29a-3p and miRNA 29b-3p, higher amounts of miRNA29c-3p were associated with a shorter overall survival specifically among patients diagnosed with a HER2+ breast cancer.

Example 4 miRNA 200 Family: Serum Expression Level as a Function of Her2 Status and Survival Analyses of Patients with Breast Cancer Materials and Methods Overall survival: The effect of miRNA 200 family level of expression on the overall survival of breast cancer patients was measured using the online miRpower Kaplan-Meier plotter (kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ER) or performed on HER2− (Triple negative breast cancers (TNBC) molecular subtype) breast cancer patients.

Serum Levels of Circulating miRNA 200 Family:

MiRNA expression levels in pre-operative serum samples quantified by qRT-PCR derived from healthy individuals (n=22), HER2+ breast cancer patients (n=14) or HER2− breast cancer patients (n=18) obtained from the study GSE42128 (Gene Expression Omnibus accession number) on array express database (www.ebi.ac.uk/arrayexpress/) were analyzed. The combined profile of their expression is the mean of their individual expression. Statistical analysis is a Kruskal-Wallis one-way anova test (P=0.0174; Dunn's multiple comparisons test: Healthy vs. HER2+ adjusted P=0.0255 *; Healthy vs. HER2− adjusted P>0.9999 ns; HER2+ vs. HER2− adjusted P=0.0463 °) performed using GraphPad Prism software.

Results

Survival expectancy analyses: Among the 5 members of miR200 family, miR200a-3p (FIG. 3 A, F), miRNA 200c-3p (FIG. 3 C, H) and miRNA 141-3p (FIG. 3 D, I) levels of expression did not significantly impacted patients' survival. On the contrary, high expression levels of miRNA 200b-3p and miRNA 429-3p were associated with a significantly shorter overall survival compared to patients having low expression level of these 2 miRNAs (FIG. 3 B, E).

MiRNA 2006-3p:
Median survival: 62 months with high expression level of miRNA 200b-3p vs. more than 120 months with low expression level of miRNA 200b-3p,
Overall survival: 60% death with high expression level of miRNA 200b-3p compared to 20% with low expression level of miRNA 200b-3p (P=0.078).

MiRNA 429-3p:
Median survival: 62 months with high expression level of miRNA 429-3p vs. more than 120 with low expression level of miRNA 429-3p months,
Overall survival: 60% death with high expression level of miRNA 429-3p compared to 20% with low expression level of miRNA 200b-3p (P=0.09).

This trend was specific of HER2+ breast cancers since level of expression of these miRNAs did not significantly alter survival profiles of HER2− breast cancer patients (miRNA 200b-3p: P=0.38; miRNA 429-3p: P=0.13) (FIG. 3 G, J).

Survival analyses therefore demonstrate that higher amounts of miRNA 200b-3p and miRNA 429-3p are associated with a shorter overall survival specifically among patients diagnosed with a HER2+ breast cancer.

Serum Level Comparisons between HER2+ Breast Cancer Patients and Non-Diseased Subjects:

Individual level of expression of miR-141-3p, miR-200a-3p, miR-200b-3p and miR-200c-3p in pre-operative serum samples of HER2+ breast cancer patients (n=14) were found higher compared to HER2− breast cancer patients (n=18) or healthy controls (n=22) (FIG. 27A). The combined expression level of miR-141-3p, miR-200a-3p, miR-200b-3p and miR-200c-3p is significantly higher in serum samples from HER2+ breast cancer patients than HER2− breast cancer patients (P=0255) or healthy controls (P=0.0463) (FIG. 27B).

The combined amount of key miRNAs (miRNA 141-3p, miRNA 200a-3p and miRNA 200b-3p and miRNA 200c-3p) is found significantly increased in the serum of HER2+ breast cancer patients compared to HER2− breast cancer patients and healthy individuals. Therefore, they represent very interesting biomarkers for non-invasive diagnosis of breast cancer.

Conclusion:

Altogether these results point out the relevance of the miRNAs of miRNA 200 family as biomarkers in a method for diagnosing and/or prognosticating HER2-dependent cancer in a subject, and as valuable targets in HER2+ cancer therapeutic strategy.

Example 5

Survival Analyses of Patients with Breast Cancer Depending on miRNA 15 Family Level of Expression Materials and Methods The effect of miRNA 15 family level of expression on the overall survival of breast cancer patients was measured using the online miRpower Kaplan-Meier plotter (kmplot-.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ER) or performed on HER2− (Triple negative breast cancers (TNBC) molecular subtype) breast cancer patients.

Results

Among the 6 members of miRNA 15 family, high expression levels of miRNA 16-5p (FIG. 4 A), miRNA 15a-5p (FIG. 4 B), miRNA 424-5p (FIG. 4 E) and miRNA 497-5p (FIG. 4 F) were associated with a trend towards shorter overall survival compared to patients having low expression of these miRNAs.

MiRNA 16-5p:
  Median survival: 107 months with high expression level of miRNA 16-5p vs. more than 200 months with low expression level of miRNA 16-5p,
  Overall survival: more than 50% death months with high expression level of miRNA 16-5p compared to less than 40% death with low expression level of miRNA 16-5p (P=0.32).

MiRNA 15a-5p:
  Median survival: 107 months with high expression level of miRNA 15a-5p vs. more than 200 months with low expression level of miRNA 15a-5p,
  Overall survival: more than 50% death with high expression level of miRNA 15a-5p compared to less than 40% death with low expression level of miRNA 15a-5p (P=0.37).

MiRNA 424-5p:
  Median survival: 108 months with high expression level of miRNA 424-5p vs. more than 200 months with low expression level of miRNA 424-5p,
  Overall survival: more than 50% death with high expression level of miRNA 424-5p compared to less than 30% with low expression level of miRNA 424-5p (P=0.42).

MiRNA 497-5p:
  Median survival: 108 months with high expression level of miRNA 497-5p vs. more than 200 months with low expression level of miRNA 497-5p,
  Overall survival: more than 50% death with high expression level of miRNA 497-5p compared to less than 30% death with low expression level of miRNA 497-5p (P=0.42).

Moreover miRNA 424-5p (FIG. 4 K) and miRNA 497-5p (FIG. 4 L) did not alter survival profiles of HER2− breast cancer patients (P=0.79 and 0.91). In HER2− breast cancer patients, high expression level of miRNA 15a-5p (FIG. 4 H) was associated with a trend towards longer overall survival compared to patients having low expression level of this miRNA (P=0.38).

MiRNA 195-5p (FIG. 4 D) expression level did not alter survival profiles of HER2+ breast cancer patients and low expression level of miRNA 15b-5p (FIG. 4 C) that was not seen upregulated in the miRnome analysis of FIG. 1 were associated with a trend towards shorter overall survival compared to patients having high expression level of this miRNA (P=0.17).

Conclusion

Survival analyses demonstrated that higher amounts of miRNA 16-5p, miRNA 15a, miRNA 424-5p and miRNA 497-5p were associated with a shorter overall survival specifically among patients diagnosed with a HER2+ breast cancer.

Example 6

Survival Analyses of Patients with Breast Cancer Depending on miRNA 615-3p, miRNA 451a-3p and miRNA 542-5p Level of Expression Materials and Methods The effect of miRNA 615-3p, miRNA 451a-3p and miRNA 542-5p on the overall survival of breast cancer patients was measured using the online miRpower Kaplan-Meier plotter (kmplot.com/analysis/index.php?p=service&cancer=breast_miRna) on the METABRIC (1262 breast tumors). Patients were divided into two groups based on the target miRNA expression. Analyses were either performed on HER2 positive status (HER2+ by Immuno-histo chemistry (IHC) on molecular subtype HER2+ER) or performed on HER2− (Triple negative breast cancers (TNBC) molecular subtype) breast cancer patients.

Results

High levels of miRNA 451a-3p (FIG. 5 B), miRNA 542-5p (FIG. 5 C) and miRNA 615-3p (FIG. 5 A) were associated with a significantly shorter overall survival compared to patients having low expression of these 3 miRNAs.

MiRNA 615-3p:
  Median survival: 108 months with high expression level of miRNA 615-3p vs. more than 200 months with low expression level of miRNA 615-3p,
  Overall survival: more than 50% with high expression level of miRNA-615-3p death compared to less than 30% death with low expression level of miRNA 615-3p (P=0.54).

MiRNA 451a-3p:
  Median survival: 108 months with high expression level of miRNA 451a-3p vs. more than 200 months with low expression level of miRNA 451a-3p,
  Overall survival: more than 50% death with high expression level of miRNA 451a-3p compared to less than 40% with low expression level of miRNA 451a-3p (P=0.26).

MiRNA 542-5p:
  Median survival: 108 months with high expression level of miRNA 542-5p vs. more than 200 months with low expression level of miRNA 542-5p,
  Overall survival: more than 50% death with high expression level of miRNA 542-5p compared to less than 30% death with low expression level of miRNA 542-5p (P=0.31).

There trends were specific of HER2+ breast cancers since levels of expression of these miRNAs did not necessarily alter survival profiles of HER2− breast cancer patients (FIG. 5 D-F).

Conclusion

Survival analyses demonstrated that higher amounts of miRNA 615-3p, miRNA 451a-3p and miRNA 542-5p were

Example 7

Role of miRNA 29c-3p on HER2 Expression and Activation in SKBR3 Cell Line and MDAMB231 Cell Line Materials and Methods According to the methods detailed in Example 1, 20 or 40 nM of anti-miR29c-3p (Active Motif, INH0080) (antagomiR) was transfected 48 h, 72 h or 96 h in SKBR3, a HER2+ breast cancer cell line, and HER2 activation (pYHER2) and expression (HER2) as well Clathrin level of expression were analyzed by western blot (FIG. 6A) and quantified (FIG. 6B and FIG. 8). At 72 h, HER2 mARN expression level was also analyzed by qRT-PCR (FIG. 9).

According to the methods detailed in Example 1 was transfected 48 h in MDAMB231, a HER2− breast cancer cell line, and HER2 activation (pYHER2) and expression (HER2) as well as Clathrin level of expression were analyzed by western blot (FIG. 7A) and quantified (FIG. 7B).

Results

To explore the role of miRNA 29c-3p on HER2 we first performed gain and loss of function experiments in SKBR3 and MDAMB231. 48 h after transfection, we observed that the anti-miRNA 29c-3p (20 nM) led to a 70% decrease in HER2 activation accompanied by a 50% decrease of HER2 expression (FIG. 6). On the contrary, the miRNA 29c-3p mimic induced a 65% increase in HER2 activation accompanied by a 130% increase of HER2 expression in MDAMB231 (FIG. 7). There was no effect on MSN expression in both conditions (FIG. 6, 7). We also reported a time-dependent effect reaching 75% HER2 inhibition after 72 and 96 h of transfection (FIG. 8). A 50% decrease of HER2 expression was further confirmed at mRNA level (HER2 mRNA) by qRT-PCR in SKBR3 transfected with the anti-miRNA29c-3p (FIG. 9).

Conclusion

Anti-miR29c-3p strongly inhibited HER2 expression and activation independently of MSN expression in SKBR3 cells. Conversely, ectopic expression of miRNA 29c-3p mimic in MDAMB231 conducted to increased HER2 expression and activation independently of MSN expression.

These results confirmed that an agent that modulates the activity of miRNA 29c-3p, such as anti-miRNA 29c-3p, can be used in the treatment of HER2-dependent cancer, such as HER2+ breast cancer.

Example 8

Role of miRNA 29c-3p on HER2 Expression and Activation in BT474 Cell Line

Materials and Methods

According to the methods detailed in Example 1, 20 or 40 nM of anti-miRNA 29c-3p (Active Motif, INH0080) (antagomiR) was transfected 72 h in BT474, a HER2+ breast cancer cell line, and HER2 activation (pYHER2) and expression (HER2) as well as activation of Akt (pAkt) and ERK (pERK) and Clathrin level of expression were analyzed by western blot (FIG. 10 A) and quantified (FIG. 10 B). HER2 mARN expression level was also analyzed by qRT-PCR (FIG. 11).

Additionally, 40 or 60 nM of LNA anti-miRNA 29c-3p (Qiagen, YI04105460, SEQ ID NO: 30) (LNA 29c) or 60 nM of control LNA anti-miRNA (Qiagen, YI00199006, SEQ ID NO: 33) (LNA CTA) was transfected 72 h in BT474, a HER2+ breast cancer cell line, and HER2 activation (pYHER2) and expression (HER2) as well as Clathrin expression level were analyzed by western blot (FIG. 16).

Results

To confirm the HER2 inhibition induced by the anti-miRNA 29c-3p in BT474, we used BT474 cells that exhibit high levels of activated HER2 and estrogen receptor. 72 h after transfection, we confirmed that the anti-miR29c-3p (40 nM) led to a 50% decrease in HER2 activation accompanied by a 20% decrease of HER2 expression and respectively 60% and 30% decrease in Akt and ERK activation (FIG. 10). A 20% decrease of HER2 expression was further confirmed at mRNA level by qRT-PCR (HER2 mRNA) in BT474 transfected with the anti-miR29c-3p (FIG. 11).

HER2 inhibition induced by the anti-miRNA 29c-3p was also tested using LNA-based anti-miRNA 29c-3p and negative control anti-miRNA in BT474 cells. The LNA-based anti-miR29c-3p (40 and 60 nM) led to a 30% decrease in HER2 activation accompanied by a 35% decrease of HER2 expression observed at 40 nM 72 h after transfection compared to the negative control (FIG. 16).

Conclusion

MiR29c-3p inhibitors inhibited HER2 expression and activation in BT474 cells. These results confirmed that an agent that modulates the activity of miRNA 29c-3p, such as anti-miRNA 29c-3p, can be used in the treatment of HER2-dependent cancer, such as HER2+ breast cancer.

Example 9

Role of miRNA 200 Family on HER2 Activation

Materials and Methods

According to the methods detailed in Example 1, 20, 40, 60 and 80 nM of anti-miR200b-3p (Active motif, INH0252) (FIG. 12) or 20, 40, 60, 80 and 100 nM anti-miRNA 429-3p (Active motif, INH0388). (FIG. 13) (antagomiRs) were transfected 72 h in SKBR3, a HER2+ breast cancer cell line, and HER2 activation (pYHER2) and expression (HER2) as well as the activation of ERK (pERK) and Clathrin or Ezrin level of expression were analyzed by western blot (FIG. 12 A and FIG. 13 A) and quantified (FIG. 12 B, 13 B).

Additionally, 60 nM of control LNA anti-miRNA (Qiagen, YI00199006, SEQ ID NO: 33) (LNA CTA) or 30 or 60 nM of LNA anti-miRNA 429-3p (Qiagen, YI04101290, SEQ ID NO: 32) (LNA 429) was transfected 72 h in BT474, a HER2+ breast cancer cell line, and HER2 activation (pYHER2) and expression (HER2) as well as activation of Akt (pAkt) and ERK (pERK) and Clathrin expression level were analyzed by western blot (FIG. 17).

Results

To explore the role of miRNA 200b-3p and miRNA 429-3p on HER2 we also performed gain and loss of function experiments in SKBR3. 72 h after transfection, we observed that the anti-miRNA 200b-3p induced a dose-dependent inhibition of HER2 activation reaching 40% at 80 nM whereas there was no effect on HER2 level of expression (FIG. 12). We also detected a dramatic dose-dependent inhibition of HER2 activation induced by the transfection of anti-miRNA 429-3p in SKBR3. This reached 100% inhibition at 100 nM and was accompanied by a similar decrease of HER2 expression level. Anti-miRNA 429-3p also induced a dose-dependent pERK inhibition reaching 50% (FIG. 13).

HER2 inhibition induced by the anti-miRNA 429-3p was also tested using LNA-based anti-miRNA 429-3p and negative control anti-miRNA in BT474 cells. The LNA based anti-miR429-3p (30 nM and 60 nM) led to a dose-dependent 16% and 60% decrease in HER2 activation accompanied by a 30% decrease of HER2 expression observed at 60 nM and 45% and 85% inhibition of Akt activation and 40% and 65% inhibition of ERK activation 72 h after transfection compared to the negative control (FIG. 17).

Conclusion

Among the miRNA 200 family, we demonstrated that miRNA-200b-3p reduced HER2 activation. On the other hand, we showed that miRNA 429-3p strongly inhibited HER2 expression and activation.

These results confirmed that an agent that modulates the activity of miRNA 200b-3p and miRNA 429-3p, such as anti-miRNA 200-3p and anti-miRNA 429-3p, can be used in the treatment of HER2-dependent cancer, such as HER2+ breast cancer.

Example 10

Role of miRNA 200 Family on HER2-Dependent Cell Division

Materials and Methods

According to the methods detailed in Example 1, the HER2-overexpressing BT474 or SKBR3 cancer cell lines were transfected with 40 nM of anti-miRNA 200b-3p or with 40 or 80 nM of anti-miRNA 429-3p and cells proliferation was determined after 96 h using an MTT assay. Non treated cells were included as a negative control.

Results

The results are shown in FIG. 14 and FIG. 15. The figures showed that 40 nM of anti-miRNA 200b-3p induced a significant 25% decrease in proliferation of BT474 cells at 96 h post transfection. Similarly, 40 and 80 nM of anti-miRNA 429-3p induced a significant 45% decrease in proliferation of SKBR3 cells at 96 h post transfection.

Conclusion

These results showed that anti-miRNA 200b-3p and anti-miRNA 429-3p can actively block HER2-dependent cell proliferation in HER2+ breast cancer cell lines. The effect of miRNA 429-3p inhibition was stronger than miRNA 200b-3p inhibition, in agreement with its stronger inhibition of HER2 phosphorylation (Example 8).

These results confirmed that an agent that modulates the activity of miRNA 200b-3p and miRNA 429-3p, such as anti-miRNA 200-3p and anti-miRNA 429-3p, can be used in the treatment of HER2-dependent cancer, such as HER2+ breast cancer.

Example 11

Role of miRNA 29c-3p on HER2-Dependent Cell Division using an Impedance-Based Cell Growth Assay Materials and Methods According to the methods detailed in Example 1, the HER2-overexpressing SKBR3 (FIG. 18) or BT474 (FIG. 20) cancer cell lines were transfected with 60 or 100 nM of LNA anti-miRNA 29c-3p (SEQ ID NO: 30) or with 100 nM of control LNA anti-miRNA (SEQ ID NO: 33) and cell proliferation was determined in real time during 140 h or 168 h using an impedance-based cell growth assay.

Results

The results are shown in FIG. 18 and FIG. 20. The figures show that 100 nM of LNA anti-miRNA 29c-3p induced a significant 32% decrease in proliferation of SKBR3 cells at 140 h post seeding. To a larger extent, 60 and 100 nM of anti-miRNA 29c-3p induced respectively a significant 52% and 70% decrease in proliferation of BT474 cells at 168 h post seeding.

Conclusion

These results show that LNA anti-miRNA 29c-3p can actively block HER2-dependent cell proliferation in HER2+ breast cancer cell lines.

These results therefore show that an agent that modulates the activity of miRNA 29c-3p such as LNA anti-miRNA 29c-3p, can be used in the treatment of HER2-dependent cancer, such as HER2+ breast cancer.

Example 12

Role of miRNA 200 Family on HER2-Dependent Cell Division Using Impedance Based Cell Assay Materials and Methods 60 or 100 nM of LNA anti-miRNA 200b-3p (LNA 200b, SEQ ID NO: 31) (FIG. 20 and FIG. 21) control LNA anti-miRNA (LNA CTA, SEQ ID NO: 33) or of LNA anti-miRNA 429-3p (LNA 429, SEQ ID NO: 32) (FIG. 22 and FIG. 23) was transfected in BT474 (FIG. 20 and FIG. 23) or SKBR3 (FIG. 21 and FIG. 22) cells, two HER2+ breast cancer cell lines and cell proliferation was determined in real time during 113 h, 160 or 168 h using an impedance-based cell growth assay.

Moreover, 0.1 and 1 µM phosphorothioate-modified LNA anti-miRNA 200b-3p (LNA 200b, SEQ ID NO: 31) (FIG. 24), control LNA anti-miRNA (LNA CTA, SEQ ID NO: 33) or LNA anti-miRNA 429-3p (LNA 429, SEQ ID NO: 32) (FIG. 25) were delivered in the absence of any transfection reagent in BT474 HER2+ breast cancer cell line and cell proliferation was determined in real time during 192 h using an impedance-based cell growth assay.

Results

The results show that 40 nM and 60 nM of LNA anti-miRNA 200b-3p induced a significant 25% decrease in proliferation of BT474 cells at 96 h post transfection and at 168 h post seeding. Also 100 nM of LNA anti-miRNA 200b-3p induced a significant 52% decrease in proliferation of BT474. In SKBR3 cells 60 nM of LNA anti-miRNA 200b-3p induced a significant 25% decrease in proliferation at 113 h post seeding. Similarly, 40 and 80 nM of LNA anti-miRNA 429-3p induced a significant 45% decrease in proliferation of SKBR3 cells at 96 h post transfection and 60 and 100 nM induced a significant 75% decrease in proliferation of SKBR3 cells at 160 h post seeding. In BT474 cells 60 nM and 100 nM of LNA anti-miRNA 429-3p induced respectively a significant 87% and 92% decrease in proliferation at 168 h post seeding.

Moreover, gymnotic delivery of LNA anti-miRNA 200b-3p (FIG. 24) or LNA anti-miRNA 429-3p (FIG. 25) at 0.1 µM had no effect on the proliferation of BT474 cells whereas 1 µM of LNA anti-miRNA 200b-3p induced a significant 32% decrease in proliferation of BT474 cells at 146 h post treatment. Similarly, 1 µM of LNA anti-miRNA 429-3p induced a significant 58% decrease in proliferation of BT474 cells at 146 h post treatment.

Conclusion

These results showed that LNA anti-miRNA 200b-3p and LNA anti-miRNA 429-3p can actively block HER2-dependent cell proliferation in HER2+ breast cancer cell lines with two distinct inhibitors. Moreover LNA anti-miRNA 200b-3p and LNA anti-miRNA 429-3p can be used in the absence of any transfection agent by gymnotic delivery to block HER2-dependent cell proliferation in HER2+ breast cancer cell line. The effect of miRNA 429-3p inhibition was stronger than miRNA 200b-3p inhibition, in agreement with its stronger inhibition of HER2 phosphorylation (Example 8).

These results confirmed that an agent that modulates the activity of miRNA 200b-3p and miRNA 429-3p, such as LNA anti-miRNA 200-3p and LNA anti-miRNA 429-3p, can be used in the treatment of HER2-dependent cancer, such as HER2+ breast cancer.

Example 13

No Effect of miRNA 29c-3p and miRNA 200 family on HER2-independent cell division Materials and Methods According to the methods detailed in Example 1, the HER2-negative MDAMB231 breast cancer cell line was transfected with 100 nM of LNA anti-miRNA 29c-3p (SEQ ID NO: 30), LNA anti-miRNA 200b-3p (SEQ ID NO: 31), LNA anti-miRNA 429-3p (SEQ ID NO: 32) or control LNA anti-miRNA (SEQ ID NO: 33) and cell proliferation was determined in real time during 160 h using an impedance-based cell growth assay (FIG. 25).

Results 100 nM of anti-miRNA 29c-3p, of LNA anti-miRNA 200b-3p or of LNA anti-miRNA 429-3p did not induce any significant change in proliferation of MDAMB231 cells at 160 h post seeding.

Conclusion

These results showed that anti-miRNA 29c-3p or LNA anti miRNAs of miRNA 200 family have no toxic effect on cell proliferation in HER2-negative breast cancer cell line. Anti-miRNAs of the invention constitute therefore specific therapeutic tools against Her2 dependent cancers.

The invention claimed is:

1. A method of treating a subject having HER2-dependent cancer, the method comprising administering to the subject an effective amount of an agent that modulates the activity of a micro ribonucleic acid (miRNA), said miRNA being selected from the group consisting of miRNA 429-3p, miRNA 29c-3p, miRNA 29b-3p, miRNA 200a-3p, miRNA 200b-3p, miRNA 200c-3p, miRNA 141-3p, miRNA 15a-5p, miRNA 15b-5p, miRNA 16-5p, miRNA 424-5p, miRNA 497-5p, miRNA 615-3p, miRNA 451a-5p and miRNA 542-5p, thereby treating the HER2-dependent cancer.

2. The method of claim 1, wherein said agent is an anti-miRNA or a miRNA mimic.

3. The method of claim 2, wherein said anti-miRNA is selected from the group consisting of anti-miRNA 429-3p, anti-miRNA 29c-3p, anti-miRNA 200a-3p, anti-miRNA 200b-3p, anti-miRNA 200c-3p, anti-miRNA 497-5p, anti-miRNA 615-3p, anti-miRNA 451a-5p and anti-miRNA 542-5p, anti-miRNA 15a-5p, anti-miRNA 16-5p and anti-miRNA 424-5p.

4. The method of claim 2, wherein said anti-miRNA is an antisense compound which targets the miRNA.

5. The method of claim 4, wherein said antisense compound comprises a contiguous nucleotide sequence complementary to a corresponding sequence of the miRNA.

6. The method of claim 4, wherein said antisense compound comprises a contiguous nucleotide sequence complementary to the full-length miRNA.

7. The method of claim 4, wherein at least 80% of the nucleotides of the antisense compound are locked nucleic acids (LNA) nucleotides.

8. The method of claim 7, wherein the locked nucleic acids (LNA) nucleotides are LNA anti-miRNA 29c-3p, LNA anti-miRNA 429-3p or LNA anti-miRNA 200b-3p.

9. The method of claim 2, wherein said miRNA mimic is selected from the group consisting of miRNA 29b-3p mimic and miRNA 15b-5p mimic.

10. The method of claim 1, wherein said HER2-dependent cancer is selected from the group consisting of breast cancer, female genital tract cancer, such as endometrial cancer, uterine cancer or ovarian cancer, bladder cancer, anal cancer, colorectal cancer, in particular uterine serous cancer, such as uterine papillary serous carcinoma, lung cancer, in particular non-small-cell lung cancer, liver cancer, kidney cancer, gastroesophageal cancer, stomach cancer, pancreas cancer and gastric cancer.

11. The method of claim 1, wherein said HER2-dependent cancer is HER2+ breast cancer.

12. The method of claim 10, wherein said breast cancer is Moesin negative.

* * * * *